US011369357B1

(12) United States Patent
Mazzolino et al.

(10) Patent No.: US 11,369,357 B1
(45) Date of Patent: Jun. 28, 2022

(54) THORACIC STRUCTURE ACCESS APPARATUS, SYSTEMS AND METHODS

(71) Applicants: Gustavo Ignacio Mazzolino, Port Saint Lucie, FL (US); Federico Jose Benetti Rossi, Rosario (AR)

(72) Inventors: Gustavo Ignacio Mazzolino, Port Saint Lucie, FL (US); Federico Jose Benetti Rossi, Rosario (AR)

(73) Assignee: InVita Science Corp., Port St. Lucie, FL (US)

( * ) Notice: Subject to any disclaimer, the term of this patent is extended or adjusted under 35 U.S.C. 154(b) by 0 days.

(21) Appl. No.: 17/553,992

(22) Filed: Dec. 17, 2021

Related U.S. Application Data

(60) Provisional application No. 63/199,780, filed on Jan. 25, 2021.

(51) Int. Cl.
 *A61B 17/02* (2006.01)

(52) U.S. Cl.
 CPC .. *A61B 17/0206* (2013.01); *A61B 2017/0237* (2013.01)

(58) Field of Classification Search
 CPC ............... A61B 17/0206; A61B 2017/0237
 USPC .................................... 600/201–245
 See application file for complete search history.

(56) References Cited

U.S. PATENT DOCUMENTS

| 4,829,985 A | * | 5/1989 | Couetil | A61B 17/0206 600/234 |
| 4,852,552 A | * | 8/1989 | Chaux | A61B 17/0206 600/234 |
| 6,199,556 B1 | * | 3/2001 | Benetti | A61B 17/02 606/198 |

* cited by examiner

*Primary Examiner* — Eduardo C Robert
*Assistant Examiner* — Tara Rose E Carter
(74) *Attorney, Agent, or Firm* — Francis Law Group

(57) ABSTRACT

A thoracic structure access system for retracting biological tissue and providing access to internal biological structures; particularly, intrathoracic structures, e.g., the heart and internal mammary arteries, to facilitate entry through the biological tissue with surgical instruments and interaction of the surgical instruments with the intrathoracic structures during a thoracic surgical procedure; particularly, minimally invasive CAGB and OPCAB procedures. The system facilitates coronary artery bypass graft (CAGB and OPCAB) procedures via a simple incision at a transxiphoid incision site and, hence, without fully transecting the sternum, i.e., performing a full sternotomy, or performing a thoracotomy. The system includes modular retractor and retention arm assemblies in communication with a ratchet assembly. When the system is disposed proximate a transxiphoid incision site and the modular retractor and retention arm assemblies are releasably engaged to opposing biological tissue portions at the transxiphoid incision site, the ratchet assembly can be actuated to apply opposing forces to the biological tissue portions to provide an access space at the transxiphoid incision site.

1 Claim, 12 Drawing Sheets

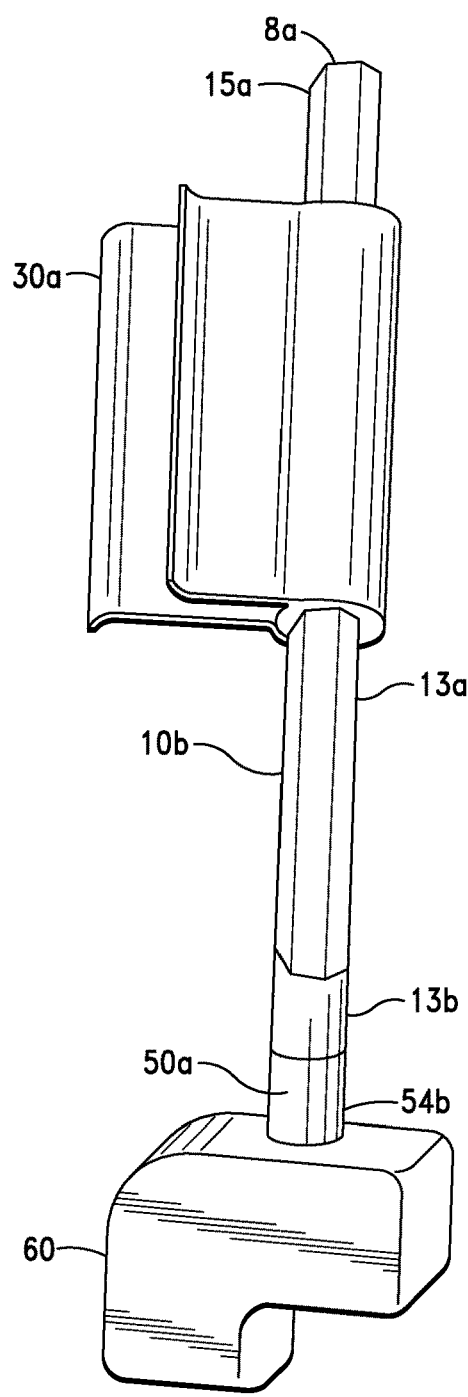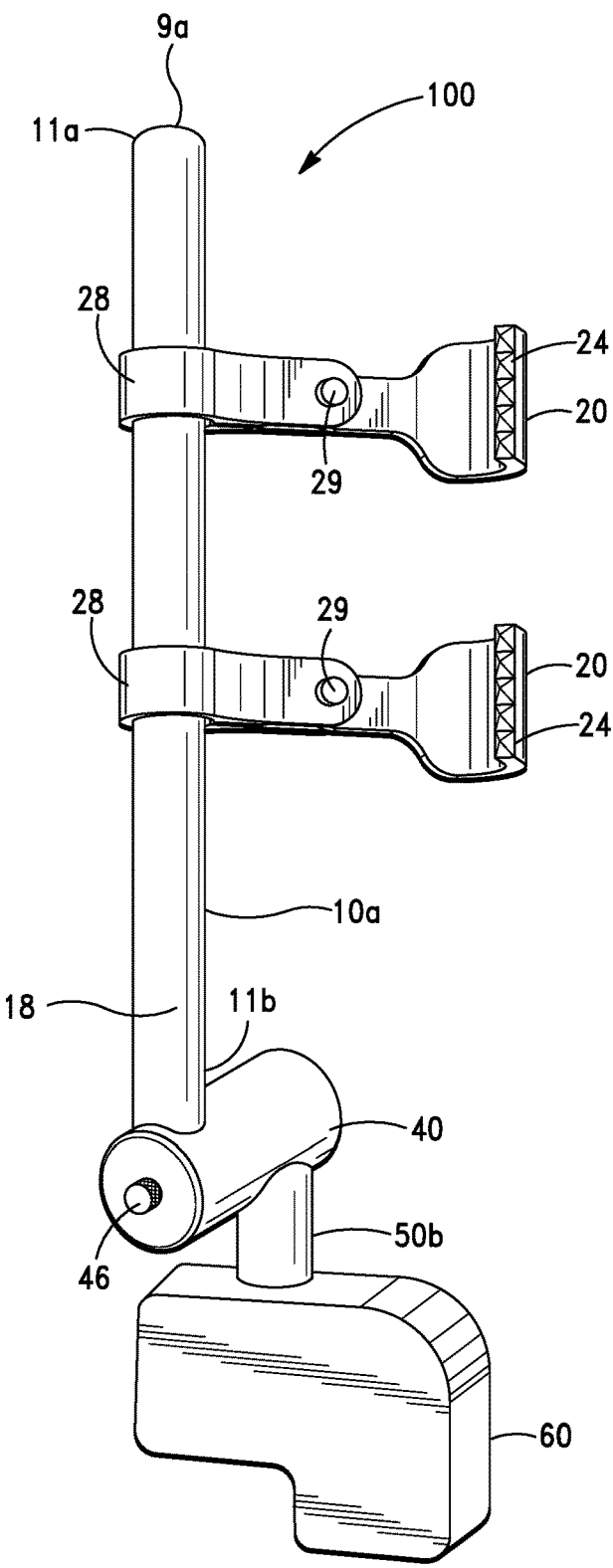
FIG. 2B
FIG. 2C

THORACIC STRUCTURE ACCESS APPARATUS, SYSTEMS AND METHODS

CROSS-REFERENCES TO RELATED APPLICATIONS

This application claims the benefit of U.S. provisional patent application Ser. No. 63/199,780, filed Jan. 25, 2021.

FIELD OF THE INVENTION

The present invention relates to apparatus, systems and methods for accessing internal biological structures. More particularly, the present invention relates to thoracic structure access apparatus and systems, and minimally invasive methods employing same for accessing internal biological structures; particularly, intrathoracic structures at a transxiphoid incision site.

BACKGROUND OF THE INVENTION

It is well established that coronary artery disease (CAD); particularly, CAD associated with atherosclerosis of coronary arteries, is one of the most common major cardiovascular diseases affecting the global human population. CAD continues to be a predominant cause of death in both developed and non-developed countries. In 2015, approximately 110 million people were afflicted with CAD worldwide, and approximately 8.9 million died due to medical complications associated with CAD.

CAD characterized by atherosclerosis of one or more coronary arteries typically results in restricted and, hence, insufficient blood flow to the myocardium of the heart. In severe cases of CAD, acute restriction or a complete obstruction of blood flow through one or more coronary arteries can, and often will result in myocardial infarction, i.e., heart failure.

Various procedures have thus been developed to treat CAD. One of the most common non-endovascular procedures for treating CAD comprises coronary artery bypass grafting (CABG), which involves excising an autologous blood vessel, e.g., an internal mammary artery, radial artery, and/or greater saphenous vein, from a pre-determined region of a subject's body for use as a vessel bypass graft to route blood flow distally to an obstructed region of a coronary artery.

As is well known in the art, conventional CABG procedures typically require opening the chest wall via a full sternotomy, and stopping a subject's heart and supporting the subject's cardiovascular system with a cardiopulmonary bypass (CPB) system.

As is also well known in the art, the above noted procedure steps associated with conventional CABG procedures are highly invasive, pose significant risk of operative complication and patient mortality, require lengthy hospitalization and are expensive with regards to short term and long-term treatment costs.

In an effort to address the above noted drawbacks associated with conventional CABG procedures, "minimally invasive" CABG procedures, i.e., CABG procedures that do not require opening the chest wall via a sternotomy and/or supporting the subject's cardiovascular system with a CPB system, have thus been developed. Such minimally invasive CABG procedures include off-pump coronary artery bypass (OPCAB) procedures, minimally invasive direct coronary artery bypass (MIDCAB) procedures, and the MINI off-pump coronary artery bypass (MINI OPCAB) procedure described in detail in U.S. Pat. No. 6,199,556, which was developed by Applicants.

Although conventional minimally invasive CABG procedures, including OPCAB, MIDCAB and MINI OPCAB procedures, address most of the major drawbacks and disadvantages associated with such procedures, as discussed in detail below, there are still several major drawbacks and disadvantages associated with conventional minimally invasive CABG procedures.

A major drawback and, hence, disadvantage associated with an OPCAB procedure is that, although the procedure does not require stopping the heart and supporting the subject's cardiovascular system with a CPB system, a full thorax transection, i.e., full sternotomy, is still required.

A major drawback and, hence, disadvantage associated with MIDCAB procedures is that such procedures often require an incision to be made in the thorax between a subject's ribs or intercostal cartilage (i.e., a thoracotomy), which are often retracted to provide a surgeon with access to a subject's intrathoracic structures. The formation and retraction of thoracotomies is often associated with some of the same post-surgical maladies exhibited in subjects who have undergone a sternotomy, including severe post-surgical pain and respiratory complications.

Since MIDCAB procedures often employ robotic systems, further drawbacks and disadvantages associated with such procedures include substantial upfront cost of specialized robotic equipment and instruments and substantial technical complexity with regards to robotically assisted techniques and associated thoracoscopic techniques, which often require considerable additional training for surgeons. Surgeons also often struggle with the lack of haptic feedback associated with robotically assisted techniques and associated thoracoscopic techniques, limiting working centers and surgical procedures.

MINI OPCAB procedures, such as disclosed in U.S. Pat. No. 6,199,556, substantially reduce and, in some instances, eliminate the above referenced major drawbacks associated with OPCAB and MIDCAB procedures. However, although MINI OPCAB procedures reduce and, in some instances, eliminate the above referenced major drawbacks associated with OPCAB and MIDCAB procedures, there are still several drawbacks associated with MINI OPCAB procedures.

As discussed in detail below, MINI OPCAB procedures employ a thoracic structure access apparatus (commonly referred to as a "retractor") to provide access to a thoracic cavity or opening at a transxiphoid incision site (also deemed and referred to herein as "a lower partial sternotomy site").

Since conventional thoracic structure access apparatus, such as disclosed in U.S. Pat. Nos. RE34,150 and 4,627,421, are specifically designed and configured for full thoracic transections, such access systems can, and often will, apply excessive forces to biological tissue proximate a transxiphoid incision site. The excessive forces can, and often will, traumatize tissue and, thereby, associated biological structures proximate the transxiphoid incision site.

Indeed, the continuous application of excess forces to biological tissue proximate a transxiphoid incision site by a thoracic structure access apparatus can, and often will, induce ischemia of the biological tissue proximate to and distant from the transxiphoid incision site due to elevated tissue pressure and/or compressed nerves and blood vessels. The thoracic structure access apparatus also traumatizes biological tissue by compressing nerves, and compressing blood vessels and, thereby, causing ischemia in biological tissues.

Such tissue and structure trauma increases the post-surgical recovery time of a patient and increases the probability of post-surgical complications, such as inflammation and/or infection of the tissue.

Further, the thoracic structure access apparatus and systems employed to perform a MINI OPCAB procedure are often cumbersome, complex, and excessively difficult for a surgeon to employ before and during a MINI OPCAB procedure.

It would thus be desirable to provide thoracic structure access apparatus and systems, and surgical procedures employing same; particularly, CABG and OPCAB procedures, which substantially reduce or eliminate the drawbacks and disadvantages associated with conventional thoracic structure access apparatus and systems, and surgical procedures employing same; particularly, CABG and OPCAB procedures.

It is therefore an object of the invention to provide improved thoracic structure access apparatus and systems, and surgical procedures employing same; particularly, CABG and OPCAB procedures, which substantially reduce or eliminate the drawbacks and disadvantages associated with conventional thoracic structure access apparatus and systems, and surgical procedures employing same; particularly, CABG and OPCAB procedures.

It is a further object of the present invention to provide thoracic structure access apparatus, systems and methods that can be readily employed to facilitate various thoracic surgical procedures in a simple and economical manner.

It is a further object of the present invention to provide thoracic structure access apparatus, systems and methods that can be readily employed to substantially reduce or eliminate trauma of biological tissue associated with tissue retraction during a surgical procedure; particularly, a CABG and/or OPCAB procedure.

It is a further object of the present invention to provide thoracic structure access apparatus and systems that facilitate CABG and OPCAB procedures via a simple incision at a transxiphoid incision site and, hence, without fully transecting the sternum, i.e., performing a full sternotomy, or performing a thoracotomy.

It is a further object of the present invention to provide thoracic structure access apparatus and systems that provide access to cardiovascular structures, including a beating heart, during a CABG and/or OPCAB procedure in a minimally invasive manner.

SUMMARY OF THE INVENTION

The present invention provides improved thoracic structure access apparatus and systems, and minimally invasive methods for accessing intrathoracic biological tissue structures of a subject via an incision (referred to herein as a "xiphoid incision" and "transxiphoid incision") at a transxiphoid incision site with same during surgical procedures; particularly, CABG and OPCAB procedures.

The thoracic structure access apparatus and systems are optimal for retracting biological tissue proximate the transxiphoid incision site and, thereby, accessing and viewing intrathoracic structures of a subject, including a subject's "beating" heart, during surgical procedures with minimal biological tissue trauma.

In one embodiment of the invention, the thoracic structure access system comprises a tissue retractor system, i.e., an offset retractor assembly, configured and adapted to provide access to cardiovascular structures via a xiphoid incision, the tissue retractor system comprising a tissue retractor arm assembly, a tissue retention arm assembly and a ratchet assembly, the tissue retractor arm assembly comprising a first longitudinal axis, the tissue retention arm assembly comprising a second longitudinal axis, the ratchet assembly comprising a third longitudinal axis, the tissue retractor arm assembly and the tissue retention arm assembly being in communication with the ratchet assembly, whereby the first longitudinal axis of the tissue retractor arm assembly and the second longitudinal axis of the tissue retention arm assembly are substantially parallel in a first position, the ratchet assembly being configured and adapted to provide at least first lateral motion of the tissue retractor arm assembly in a plane substantially parallel to the third longitudinal axis of the ratchet assembly, whereby the tissue retractor arm assembly transitions over a plurality of retractor arm tissue engaging positions when the tissue retractor arm assembly is in the communication therewith, the tissue retractor arm assembly comprising at least a first tissue retractor member configured and adapted to releasably engage first biological tissue proximate the xiphoid incision when the tissue retractor arm assembly is in at least a first retractor arm tissue engaging position of the plurality of retractor arm tissue engaging positions, the tissue retention arm assembly comprising at least a second tissue retractor member configured and adapted to releasably engage second biological tissue proximate the xiphoid incision when the tissue retention arm assembly is in a first static position and the tissue retractor arm assembly is in the at least a first retractor arm tissue engaging position, the ratchet assembly comprising a crossbar, a first ratchet sub-assembly, a second ratchet sub-assembly and a handle assembly, the first ratchet sub-assembly being connected to the tissue retractor arm assembly and comprising a first ratchet sub-assembly opening that is sized and configured to slidably receive the crossbar therein, the second ratchet sub-assembly being connected to the tissue retention arm assembly and comprising a second ratchet sub-assembly opening that is sized and configured to slidably receive the crossbar therein, the handle assembly being in communication with the first ratchet sub-assembly and adapted to induce second lateral motion of the first ratchet sub-assembly in a direction substantially parallel to the third longitudinal axis of the ratchet assembly and, thereby, the first lateral motion of the tissue retractor arm assembly.

In some embodiments, the tissue retractor arm assembly further comprises a first elongated arm member, a first coupling member and a first interconnector member, the first interconnector member comprising first and second channels, the first channel of the first interconnector member being sized and configured to slidably receive a first end of the first elongated arm member, the second channel of the first interconnector member being sized and configured to slidably receive a first end of the first coupling member, whereby, when the first elongated arm member and the first coupling member are in communication with the first interconnector member, the first elongated arm member is allowed to rotate relative to the first coupling member in a plane substantially perpendicular to the first longitudinal axis of the tissue retractor arm assembly.

In some embodiments, the tissue retention arm assembly further comprises a second elongated arm member, a second coupling member and a second interconnector member, the second interconnector member comprising third and fourth channels, the third channel of the second interconnector member being similarly sized and configured to slidably receive a first end of the second elongated arm member, the fourth channel of the second interconnector member being sized and configured to slidably receive a first end of the second coupling member, whereby, when the second elongated arm member and the second coupling member are in communication with the second interconnector member, the second elongated arm member is similarly allowed to rotate relative to the second coupling member in a plane substantially perpendicular to the second longitudinal axis of the tissue retention arm assembly.

In some embodiments of the invention, the first ratchet sub-assembly is further configured and adapted to induce rotation of the tissue retractor arm assembly in a plane substantially perpendicular to the first longitudinal axis of the tissue retractor arm assembly when the tissue retractor arm assembly is in communication with the first ratchet sub-assembly.

In some embodiments of the invention, the second ratchet sub-assembly is similarly further configured and adapted to induce rotation of the tissue retention arm assembly in a plane substantially perpendicular to the second longitudinal axis of the tissue retention arm assembly when the tissue retention arm assembly is in communication with the second ratchet sub-assembly.

In some embodiments of the invention, the first ratchet sub-assembly is further configured and adapted to induce angular articulation of the tissue retractor arm assembly relative to the first longitudinal axis of the tissue retractor arm assembly when the tissue retractor arm assembly is in communication with the first ratchet sub-assembly.

In some embodiments of the invention, the second ratchet sub-assembly is similarly further configured and adapted to induce angular articulation of the tissue retention arm assembly relative to the second longitudinal axis of the tissue retention arm assembly when the tissue retention arm assembly is in communication with the second ratchet sub-assembly.

In one embodiment, the method for accessing intrathoracic biological tissue structures of a subject generally comprises the steps of:

(i) providing the aforedescribed thoracic structure access system;

(ii) providing an incision at a transxiphoid incision site, i.e., a xiphoid incision, in the subject's sternum;

(iii) positioning the thoracic structure access system proximate the transxiphoid incision site, whereby the first tissue retractor arm sub-assembly of the tissue retractor arm assembly releasably engages first biological tissue proximate the xiphoid incision and the second tissue retractor arm sub-assembly of the tissue retention arm assembly releasably engages opposing second biological tissue proximate the xiphoid incision; and (vi) actuating the ratchet assembly to laterally translate the tissue retractor arm assembly in a first direction substantially parallel to the longitudinal axis of the ratchet assembly, whereby the tissue retractor arm assembly and tissue retention arm assemblies apply opposing forces to the first and second biological tissue proximate the xiphoid incision and provide an opening at the transxiphoid incision site.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 2B is a front plan view of the tissue retention arm assembly of the thoracic structure access system shown in FIG. 2A, in accordance with the invention;

FIG. 2C is a front plan view of the tissue retractor arm assembly of thoracic structure access system shown in FIG. 2A, in accordance with the invention;

DETAILED DESCRIPTION OF THE PREFERRED EMBODIMENT

Figure 1A:
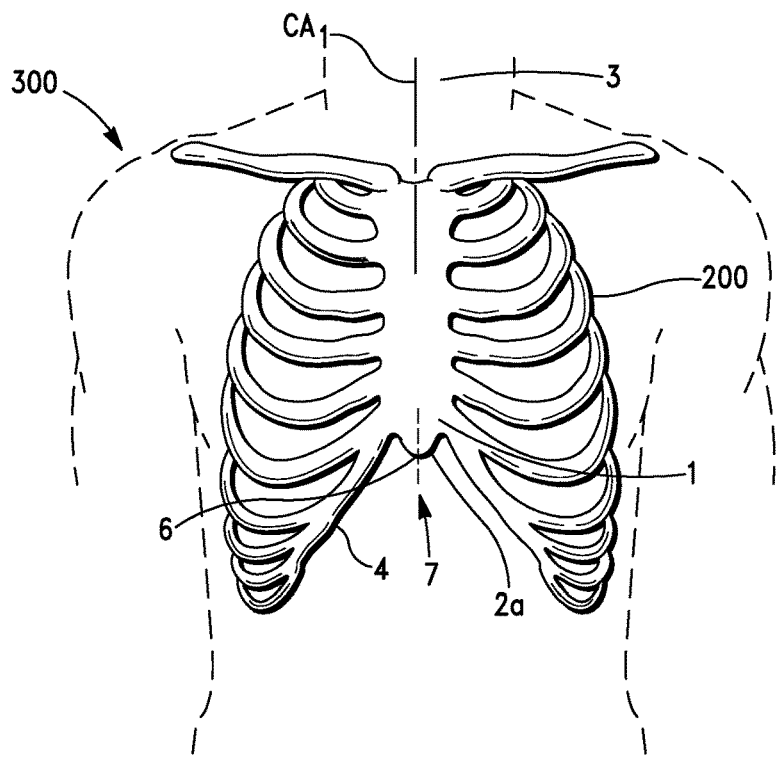
FIG. 1A is an illustration of a subject's thorax showing a transxiphoid incision site and a xiphoid incision therein.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with coronary artery bypass grafting (CABG and OPCAB) procedures; particularly, MINI off-pump coronary artery bypass (MINI OPCAB) procedures, the invention is not limited to such procedures. According to the invention, the apparatus, systems and methods of the invention can also be employed to provide access to internal structures; particularly, intrathoracic structures at a transxiphoid incision site during other surgical procedures, e.g., ventricle restoration, heart valve replacement procedures, etc.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "tissue" and "biological tissue" are used interchangeably herein, and mean and include mammalian biological tissue, such as, by way of example, pleural tissue and cardiac tissue.

The term "minimally invasive", as used herein in connection with coronary artery bypass grafting; particularly, a CABG and OPCAB procedure, means and includes a CABG and/or OPCAB procedure that does not comprise the step of fully transecting the sternum or thorax of a subject, i.e., performing a full sternotomy. The term "minimally invasive" also means and includes CABG and OPCAB procedures that do not comprise the steps of stopping a subject's beating heart and supporting the subject's cardiovascular system with a cardiopulmonary bypass (CPB) device.

The terms "xiphoid incision" and "transxiphoid incision" are used interchangeably herein, and mean and include a surgical incision proximate to, but not necessarily directly above, the xiphoid appendage (also referred to herein as a "xiphoid process") of a subject's sternum. The terms "xiphoid incision" and "transxiphoid incision" thus mean and include a "lower partial sternotomy incision".

The term "transxiphoid incision site", as used herein, thus, means and includes a surgical field proximate a subject's thorax, which provides access to intrathoracic biological tissue structures of a subject via, for example, a "xiphoid incision".

The term "retraction", as used herein, means and includes the drawing apart of or parting of incised or transected biological tissue to provide access to internal biological structures concealed by the biological tissue. The term "retraction", thus, in some instances, means and includes the drawing apart of or parting of thoracic tissue proximate a "transxiphoid incision site" to provide access to intrathoracic structures, e.g., a subject's heart.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to thoracic structure access apparatus, systems and methods for accessing internal biological structures; particularly, intrathoracic structures at a transxiphoid incision site.

More particularly, the present invention is directed to improved thoracic structure access apparatus and systems (also referred to as offset retractor assemblies) and methods for performing CABG and/or OPCAB procedures; particularly, MINI off-pump coronary artery bypass (MINI OPCAB) procedures.

In a preferred embodiment of the invention, the MINI OPCAB procedure developed by Applicants and disclosed in U.S. Pat. No. 6,199,556, which is expressly incorporated by reference herein, facilitates CABG and OPCAB procedures via a simple xiphoid incision, as defined herein (denoted "6" in FIG. 1A) at a transxiphoid incision site (denoted "7" in FIG. 1A) and, hence, without fully transecting the sternum, i.e., performing a full sternotomy or performing a thoracotomy. Access to and optimal visibility of a subject's "beating" heart at the transxiphoid incision site 7 during a MINI OPCAB procedure is achieved via a thoracic structure access apparatus and/or system.

Although conventional thoracic structure access apparatus and systems can be employed to perform minimally invasive CABG and OPCAB procedures, including MINI OPCAB procedures, as indicated above, such apparatus and systems are fraught with major drawbacks and disadvantages; particularly, a high risk of traumatized biological tissue and/or structures proximate to the transxiphoid incision site 7.

In view of the numerous drawbacks and disadvantages associated with conventional thoracic structure access apparatus and systems (and, hence, CABG and OPCAB procedures performed therewith), Applicants developed the xiphoid access apparatus and systems disclosed in U.S. Pat. No. 6,199,556.

Although the noted xiphoid access apparatus and systems, when employed properly, substantially reduce and, in many instances, eliminate the major drawbacks and disadvantages associated with conventional thoracic structure access apparatus and systems (and, thereby, CABG and OPCAB procedures performed therewith); particularly, the high risk of traumatized biological tissue and/or structures proximate to the transxiphoid incision site 7, as discussed below, there remains several drawbacks associated with the noted xiphoid access apparatus and systems.

A significant drawback associated with the xiphoid access apparatus and systems is that the noted apparatus and systems are generally cumbersome and complex, and, thus, excessively difficult for a surgeon to employ properly before and during a CABG and OPCAB procedure; particularly a MINI OPCAB procedure, which can, and often will, increase the risk of post-surgical complications, such as inflammation and/or infection of tissue, and, hence, post-surgical recovery time.

Indeed, it has been found that when the noted xiphoid access apparatus and systems are not employed properly, e.g., incorrectly mated to a subject's body, the tissue retraction arms of the xiphoid access apparatus can, and often will, traumatize biological tissue and structures, such as the costal cartilage, proximate a transxiphoid incision site 7 during tissue retraction.

The risk of incorrect mating of the noted xiphoid access apparatus and systems to a subject's body is exacerbated by virtue of the xiphoid access apparatus and systems requiring multiple ex situ or external mounting or securing points on one or more anatomical regions of a subject's body, such as the anatomical regions proximate the abdomen and the iliac crests of the subject. The xiphoid access apparatus and systems must thus be properly configured to accommodate the various sizes and configurations of a subject's body each time the xiphoid access apparatus and/or system are employed.

As will be readily apparent to one skilled in the art, the present invention provides improved thoracic structure access apparatus and systems (and, hence, CABG and OPCAB procedures employing same), which substantially reduce and, in several instances, eliminate the seminal drawbacks and disadvantages discussed above that are associated with conventional thoracic structure access apparatus and systems, as well as xiphoid access apparatus and systems disclosed in U.S. Pat. No. 6,199,556.

The thoracic structure access apparatus and systems (and, hence, minimally invasive CABG and OPCAB procedures employing same) of the invention are optimal for retracting biological tissue proximate a transxiphoid incision site and, thereby, accessing and viewing intrathoracic structures of a subject, including a subject's "beating" heart, during a CABG procedure with minimal biological tissue trauma.

In a preferred embodiment, the thoracic structure access apparatus and systems of the invention are adjustable and modular, i.e., comprise interchangeable components, and, thus, can be readily adapted to accommodate various sizes and dimensions of thoracic incision sites, more preferably, transxiphoid incision sites.

The adjustability and modularity of the thoracic structure access apparatus and systems of the invention provide a surgeon with significantly greater control with regards to the position of biological tissue pressure points proximate a transxiphoid incision site and the degree of force/pressure applied to the biological tissue pressure points.

According to the invention, the thoracic structure access systems of the invention can also be configured to accept a myriad of conventional complementary surgical attachments including, without limitation, beating heart stabilizers, mist blowers, suction tubes, suction stabilizer tubes, suture retainment members or hooks, surgical lights and optical equipment, e.g., endoscopes.

As indicated above, although the present invention is particularly applicable to minimally invasive CABG and OPCAB procedures, and, hence, is described and illustrated in connection therewith; particularly, MINI OPCAB procedures, the invention is not limited to such procedures. According to the invention, the thoracic structure access apparatus and systems of the invention can also be employed to facilitate other surgical procedures, such as, by way of example, heart valve replacement procedures.

Figure 2A:
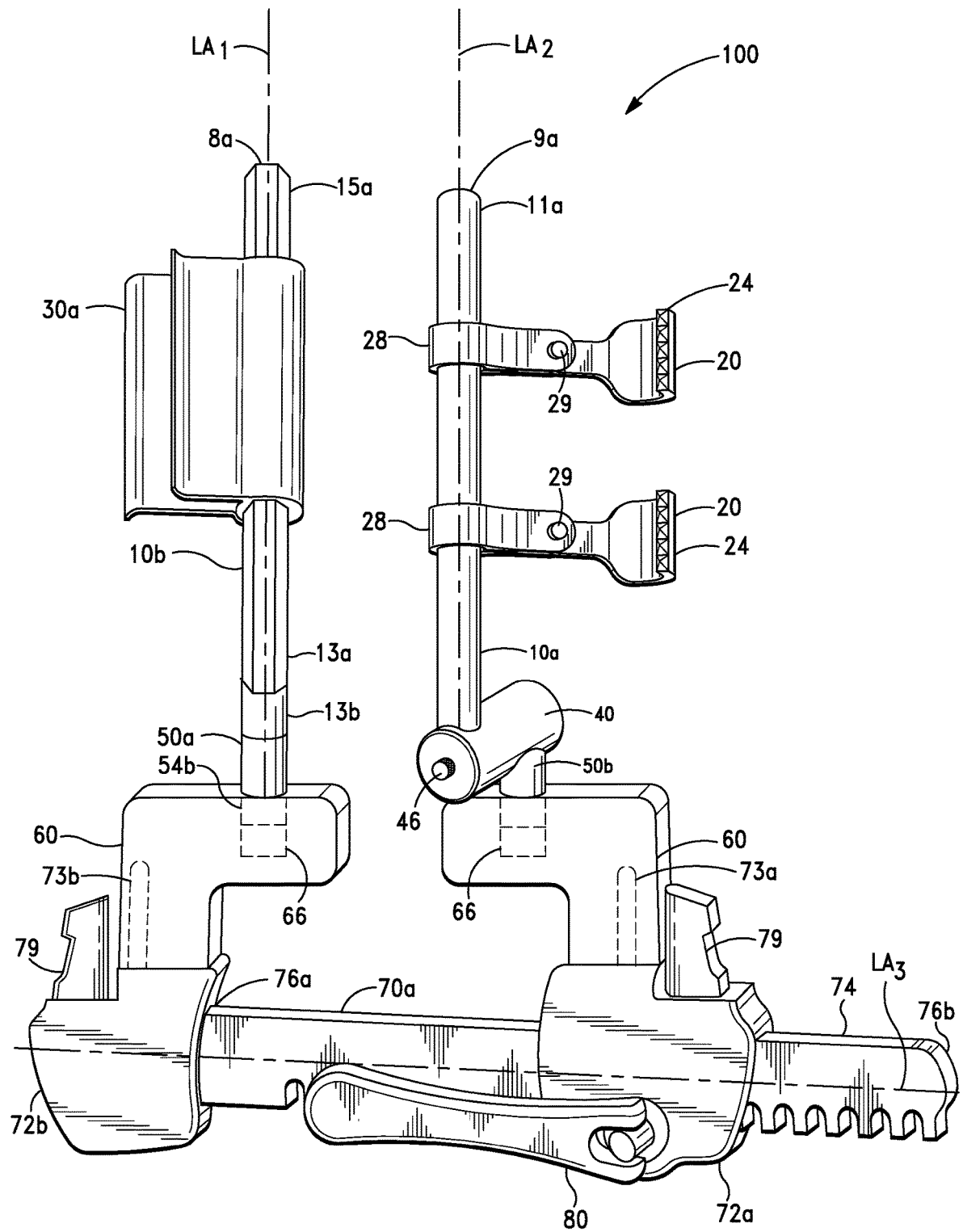
FIG. 2A is a front plan view of one embodiment of a thoracic structure access system, in accordance with the invention.

Referring now to FIG. 2A, there is shown one embodiment thoracic structure access system of the invention (denoted "100"). As illustrated in FIG. 2A, the thoracic structure access system 100 comprises a modular structure comprising a pair of arm assemblies, i.e., a retractor arm assembly 9a and a retention arm assembly 8a (also referred to herein as a "tissue retractor arm assembly" and "tissue retention arm assembly"), which are operatively connected to at least one arm assembly transverse motion inducing means, such as ratchet assembly 70a.

As indicated above and discussed in detail herein, the thoracic structure access system 100 is designed and configured to provide access to cardiovascular structures, including a beating heart, during thoracic surgical procedures; particularly, CABG and OPCAB procedures, via a simple incision at a transxiphoid incision site, such as transxiphoid incision site 7 shown in FIG. 1A, i.e., minimally invasively.

Figure 1B:
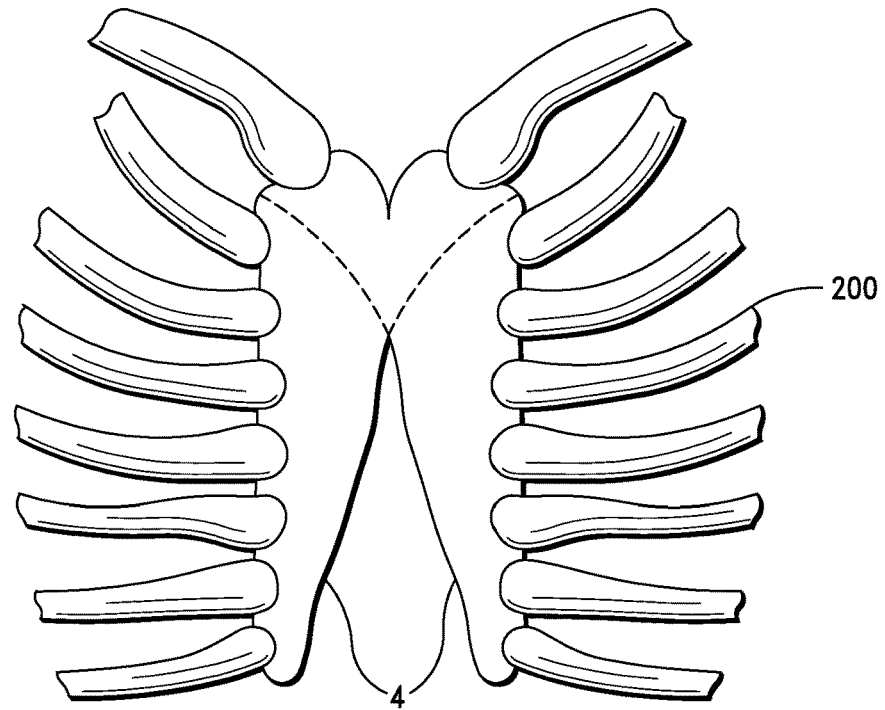
FIG. 1B is a further illustration of a subject's thorax showing a transxiphoid incision site with the lower and middle portion of the sternum spread and lifted.

In a preferred embodiment, the thoracic structure access system 100 (also referred to herein as "tissue retractor system") is specifically designed and configured to spread and lift at least the lower portion 4 of the sternum 200, as shown in FIG. 1B, with minimal biological tissue trauma.

Figure 2D:
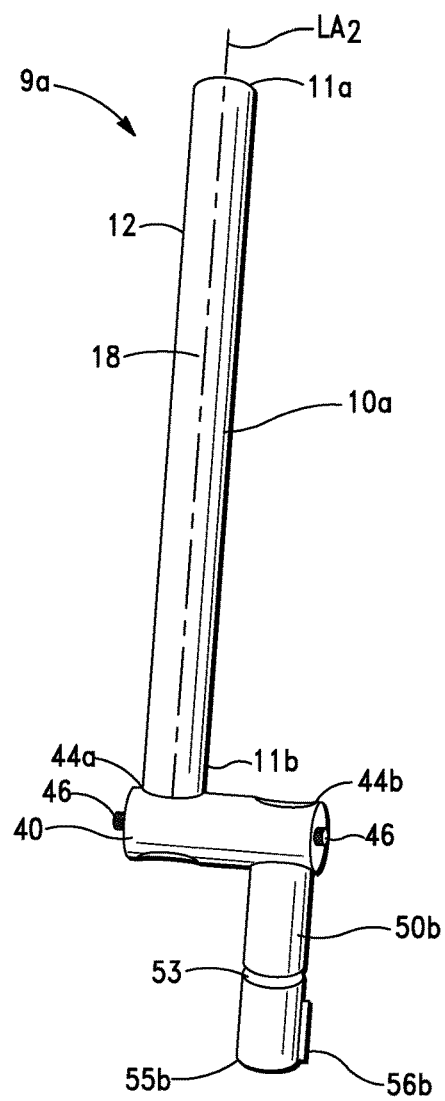
FIG. 2D is a further front plan view of the tissue retractor arm assembly shown in FIG. 2C; in accordance with the invention.

Referring now to FIGS. 2C and 2D, the retractor arm assembly 9a comprises an elongated arm member 10a (referred to in priority U.S. provisional Pat. App. No. 63/199,780 as a "rod arm" and "round rod arm"), an interconnector (or butterfly) member 40 and a coupling member 50b.

As illustrated in FIGS. 2C and 2D, in a preferred embodiment, the elongated arm member 10a comprises a rod structure or member 12 comprising a cylindrical cross-sectional shape and proximal and distal ends, 11a, 11b, respectively.

As further illustrated in FIGS. 2C and 2D, the distal end 11b of the elongated arm member 10a is preferably releasably engaged to interconnector member 40, which preferably facilitates rotation of the elongated arm member 10a in a substantially perpendicular plane relative to its longitudinal axis (denoted "$LA_2$") when the elongated arm member 10a is operatively connected to the interconnector member 40, and, as discussed below, the coupling member 50b is engaged to the base member 60 and also connected to the interconnector member 40.

In some envisioned embodiments of the invention, the interconnector member 40 comprises a structure that additionally facilitates angular articulation of the elongated arm member 10a relative to its longitudinal axis "$LA_2$", i.e., facilitates spreading of the proximal end 11a of the elongated arm member 10a.

Figure 3A:
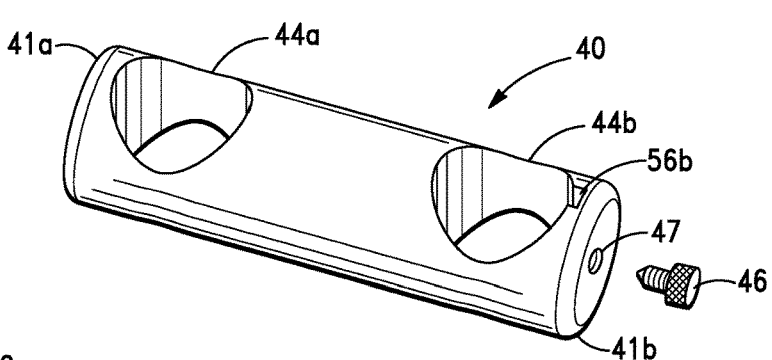
FIG. 3A is a perspective view of the interconnector member of the tissue retractor arm assembly shown in FIGS. 2A and 2D, in accordance with the invention.

In a preferred embodiment, the distal end 11b of the elongated arm member 10a is sized and configured to facilitate receipt of the distal end 11b of the elongated arm member 10a into a receiving channel of the interconnector member 40, preferably, receiving channel 44a (see FIGS. 2D and 3A).

In some embodiments, the elongated arm member 10a comprises textured features on at least a portion of the exterior surface 18 of the distal end 11b thereof to reduce the risk of accidental dislodgment of the elongated arm member 10a from interconnector member 40. According to the invention, suitable textured features include, but are not limited to, grooves and ribs.

As illustrated in FIG. 3A, in a preferred embodiment, the interconnector member 40 comprises two (2) receiving channels 44a, 44b. As illustrated in FIGS. 2C and 2D, in a preferred embodiment of the invention, receiving channel 44a is sized and configured to receive the distal end 11b of elongated arm member 10a and receiving channel 44b is sized and configured to receive the proximal end 55a of coupling member 50b.

In a preferred embodiment of the invention, the receiving channels 44a, 44b thus comprise a cylindrical cross-sectional shape that corresponds to the cylindrical cross-sectional shape of the distal end 11b of elongated arm member 10a and proximal end 55a of coupling member 50b.

According to the invention, the receiving channels 44a, 44b can also be sized and configured to receive and releasably engage any suitable elongated arm member and/or coupling member, e.g., an elongated arm member comprising a hexagonal cross-sectional shaped distal end.

In a preferred embodiment of the invention, the interconnector member 40 further comprises an arm/coupling member retention system that is configured and adapted to cooperate with the elongated arm member 10a and coupling member 50b when in communication therewith to fix the elongated arm member 10a and/or coupling member 50b at a desired position (or positions) and abate rotation of the elongated arm member 10a and coupling member 50b.

According to the invention, various conventional retention means can be employed to fix the elongated arm member 10a and/or coupling member 50b at a desired position (or positions) and abate rotation of the elongated arm member 10a and coupling member 50b when the noted components are engaged to the interconnector member 40.

Figure 3B:
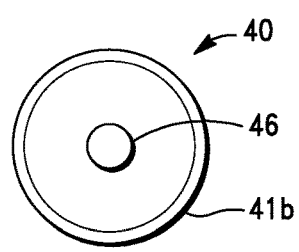
FIG. 3B is a side plan view of the interconnector member shown in FIG. 3A, in accordance with the invention.

As illustrated in FIGS. 3A and 3B, in the embodiment of the thoracic structure access system 100 shown in FIG. 2A, the interconnector member retention means comprises a set screw 46, more preferably a pair of set screws 46. In a preferred embodiment, each set screw 46 comprises a knurled head to accommodate rotation and communication thereof to the elongated arm member 10a and coupling member 50b by a surgeon.

As further illustrated in FIG. 3A, to accommodate the set screws 46, the interconnector member 40 further comprises a pair of threaded holes 47 on the proximal and distal ends 41a, 41b thereof that are sized and configured to receive and cooperate with the set screws 46.

Referring back to FIGS. 2A and 2C, the elongated arm member 10a further comprises a pair of retractor arm sub-assemblies 20 (referred to in priority U.S. provisional Pat. App. No. 63/199,780 as "hooks") that are releasably engaged to the elongated arm member 10a.

In a preferred embodiment, the retractor arm sub-assemblies 20 are sized, configured and adapted to releasably engage and retain biological tissue proximate a xiphoid incision 6 at a transxiphoid incision site 7 (as defined herein) during spreading and lifting of the lower portion 4 of the sternum 200, i.e., providing a thoracic opening or void, with the thoracic structure access system 100.

Referring now to FIGS. 4A-4D, in a preferred embodiment, the retractor arm assemblies 20 comprise a hook member 24, a looped engagement member 28 and a securement pin 29.

Figure 4A:
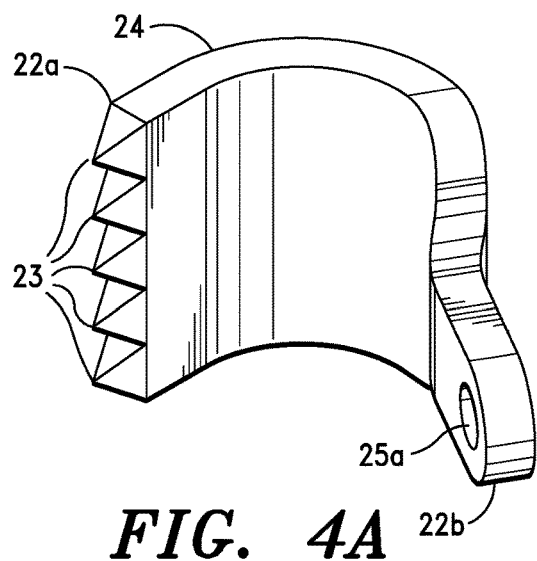
FIG. 4A is a perspective view of the hook member of the retractor arm sub-assemblies shown in FIG. 2A that is configured to engage biological tissue, in accordance with the invention.
Figure 4B:
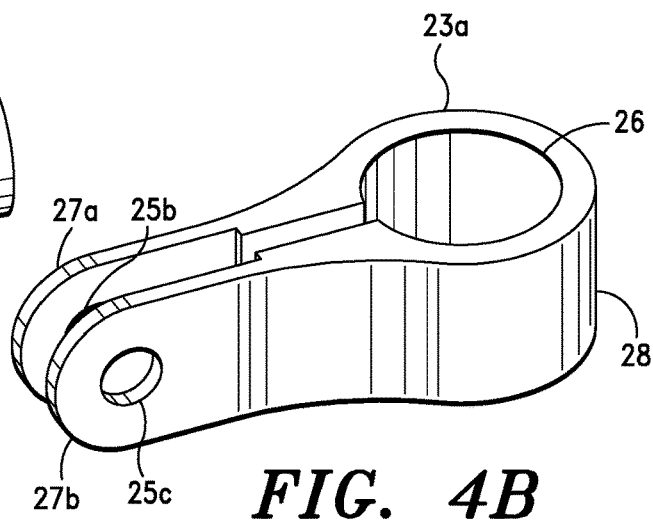
FIG. 4B is a perspective view of the looped member of the retractor arm sub-assemblies shown in FIG. 2A that is configured to engage the hook member shown in FIG. 4A to form one embodiment of a retractor arm sub-assembly, in accordance with the invention.
Figure 4C:
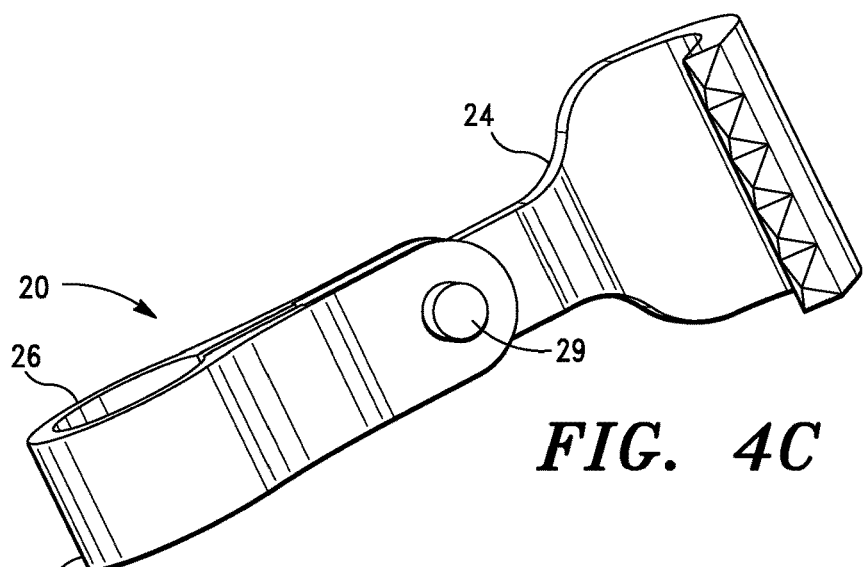
FIGS. 4C and 4D are perspective views of the retractor arm sub-assemblies shown in FIG. 2A comprising the hook member shown in FIG. 4A and looped member shown in FIG. 4B, in accordance with the invention.

As illustrated in FIGS. 4A and 4C, the hook member 24 comprises a hooked proximal end 22a and a distal engagement end 22b. The hook member 24 further preferably comprises a plurality of tissue engagement prongs or teeth 23 disposed on the hooked proximal end 22a and pin channel or opening 25a disposed on the distal attachment end 22b.

Figure 4D:
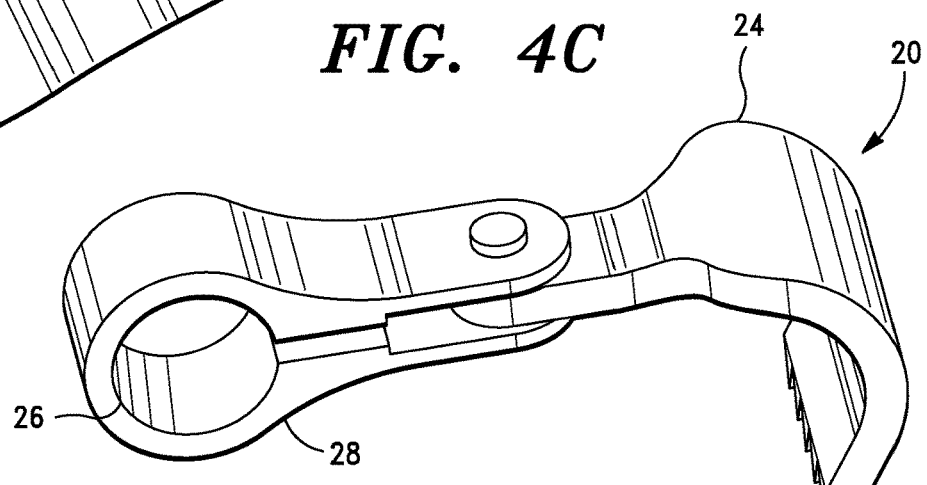

As illustrated in FIGS. 4B and 4D, the looped engagement member 28 comprises a proximal looped end 23a, a pair of distal engagement ends 27a, 27b and mating pin channels or openings 25b, 25c disposed on the distal engagement ends 27a, 27b of the looped engagement member 28.

As illustrated in FIGS. 4C and 4D, in a preferred embodiment, the distal attachment end 22b of the hook member 24 is sized and configured to be slidably received between the distal engagement ends 27a, 27b of the looped engagement member 28, and be secured therein by slidably inserting securement pin 29 through the aligned pin channels 25a, 25b, 25c.

According to the invention, the hook member 24 can also be attached to the looped engagement member 28 by other conventional attachment means, e.g., magnetic attachment means.

In some embodiments, the hook member 24 is integral with the looped engagement member 28, i.e., comprises a single member.

As illustrated in FIGS. 4B and 4D, the looped engagement member 28 further comprises an arm member receiving channel or opening 26 disposed on the looped proximal end 23a, which, as shown in FIGS. 2A and 2C, is sized and configured to slidably receive an elongated arm member of the invention, i.e., elongated arm member 10a (and elongated arm member 10b, discussed below).

According to the invention, the retractor arm assembly 9a can comprise any number of retractor arm sub-assemblies 20. In some embodiments, the retractor arm assembly 9a comprises one (1) retractor arm sub-assembly 20.

In a preferred embodiment, the retractor arm assembly 9a comprises two (2) retractor arm sub-assemblies 20, as shown in FIGS. 2A and 2C.

According to the invention, the retractor arm sub-assemblies 20 can be positioned at any suitable point along the length of the elongated arm member 10a.

As further illustrated in FIGS. 2A and 2C, in a preferred embodiment, the retractor arm assembly 9a is releasably engaged to a base member 60 via coupling member 50b.

Figure 5A:
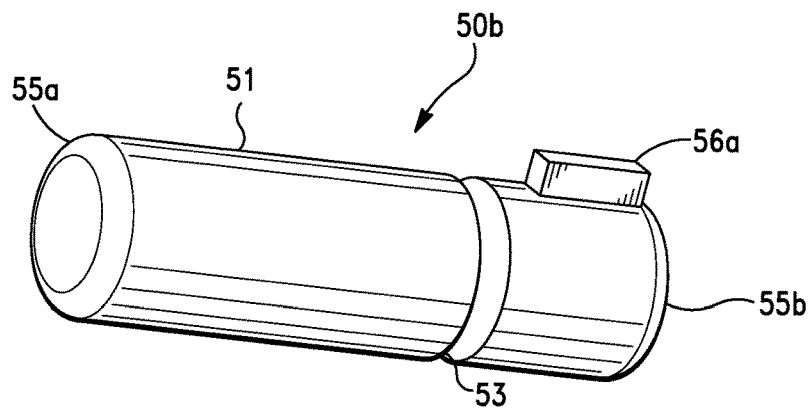
FIG. 5A is a perspective view of the retractor arm coupling member of the tissue retractor arm assembly shown in FIGS. 2A, 2C and 2D, in accordance with the invention.

Referring now to FIG. 5A, in one embodiment, the coupling member 50b (referred to in priority U.S. provisional Pat. App. No. 63/199,780 as "connector links") comprises a cylindrical member or body 51 comprising proximal and distal ends 55a, 55b, and a locking tooth 56a disposed on the distal end 55b of the coupling member 50b that is configured to prevent unwanted rotation of the coupling member 55b when engaged to the base member 60, as shown in FIGS. 2A and 2C.

As illustrated in FIG. 5A, the coupling member 50b further comprises a retainer ring or circumferential groove 53 disposed proximate the distal end 55b that is sized and configured to receive and cooperate with the arm/coupling member retention system of the base members 60, discussed below.

Figure 5B:
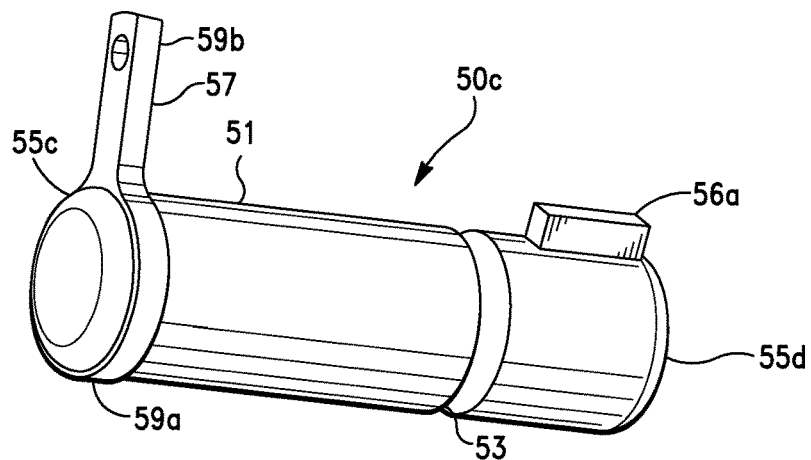
FIG. 5B is a perspective view of another embodiment of a retractor arm coupling member, in accordance with the invention.
Figure 5C:
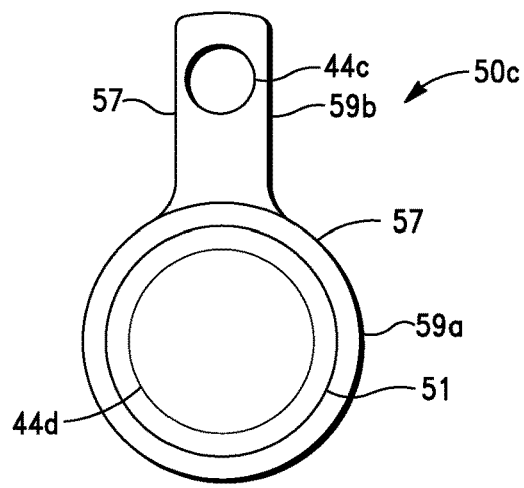
FIG. 5C is a side plan view of the retractor arm coupling member shown in FIG. 5B, in accordance with the invention.

Referring now to FIGS. 5B and 5C, there is shown a further embodiment of a coupling member of the invention (denoted "50c"). As illustrated in FIGS. 5B and 5C, the coupling member 50c similarly comprises the cylindrical body 51 of coupling member 50b; in this instance, however, the cylindrical body 51 comprises proximal and distal ends 55c, 55d. In the illustrated embodiment, the coupling member 50c further comprises an elongated interconnector structure 57 disposed on the proximal end 55c.

As further illustrated in FIGS. 5B and 5C, the interconnector structure 57 comprises a circumferential body 59a having a central hole 44d therethrough that is sized and configured to receive the proximal end 55c of the coupling member body 51 therein and an interconnector structure extension 59b that extends outwardly and, preferably, substantially parallel to the longitudinal plane defined the circumferential body 59a.

As additionally illustrated in FIG. 5C, interconnector structure extension 59b of the coupling member 50c comprises an arm receiving hole 44c that is sized and configured to slidably receive an arm member of the invention; particularly, elongated arm member 10a, and, when the arm member of the invention is engaged thereto, similarly facilitate the aforedescribed rotation of the arm member (i.e., similar to the rotation facilitated by the interconnector member 40).

Figure 6A:
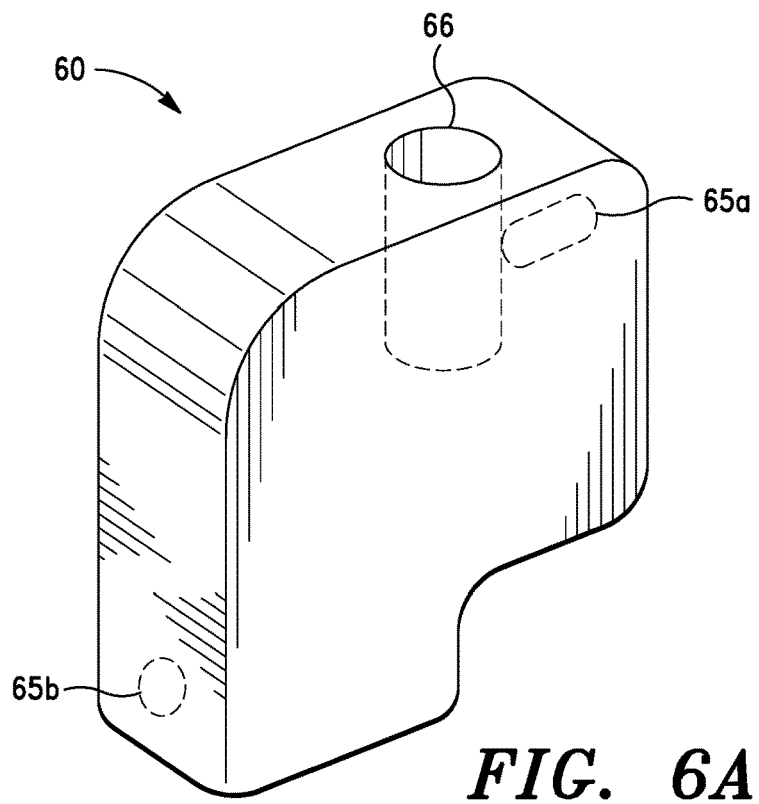
FIG. 6A is a perspective view of the base member of the thoracic structure access system shown in FIG. 2A, in accordance with the invention.
Figure 6B:
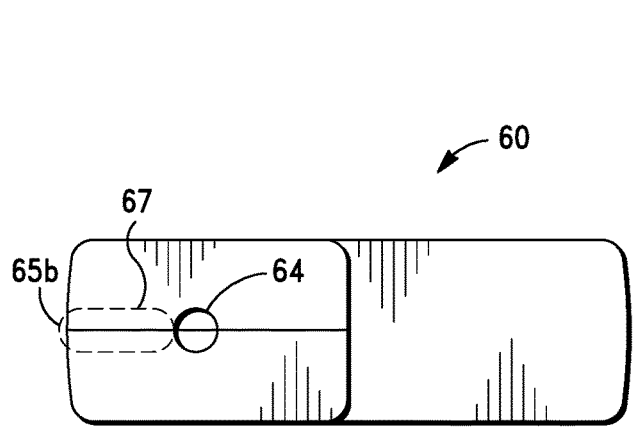
FIG. 6B is a bottom plan view of the base member shown in FIG. 6A, in accordance with the invention.
Figure 6C:
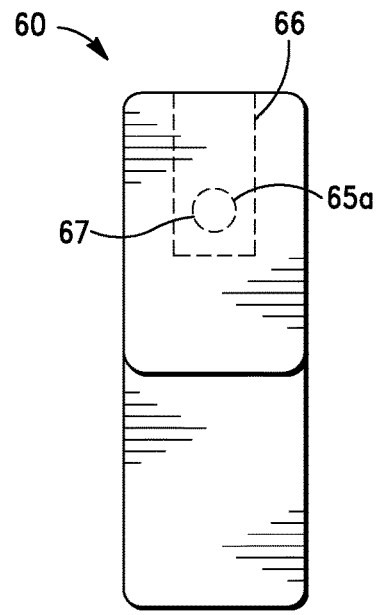
FIG. 6C is a side plan view of the base member shown in FIG. 6A, in accordance with the invention.

Referring now to FIGS. 6A-6C, the base members 60 of the thoracic structure access system 100 (referred to in priority U.S. provisional Pat. App. No. 63/199,780 as "interchangeable body component") comprise a coupling member receiving channel 66, which, as shown in FIG. 2A, is sized and configured to slidably receive the distal end 55b of the coupling member 50b and the distal end 54b of coupling member 50a, and a base member retention rod channel 64, which, as also shown in FIG. 2A and discussed below, is sized and configured to slidably receive the base member retention rods 73a, 73b of the first and second ratchet sub-assemblies 72a, 72b.

Figure 11A:
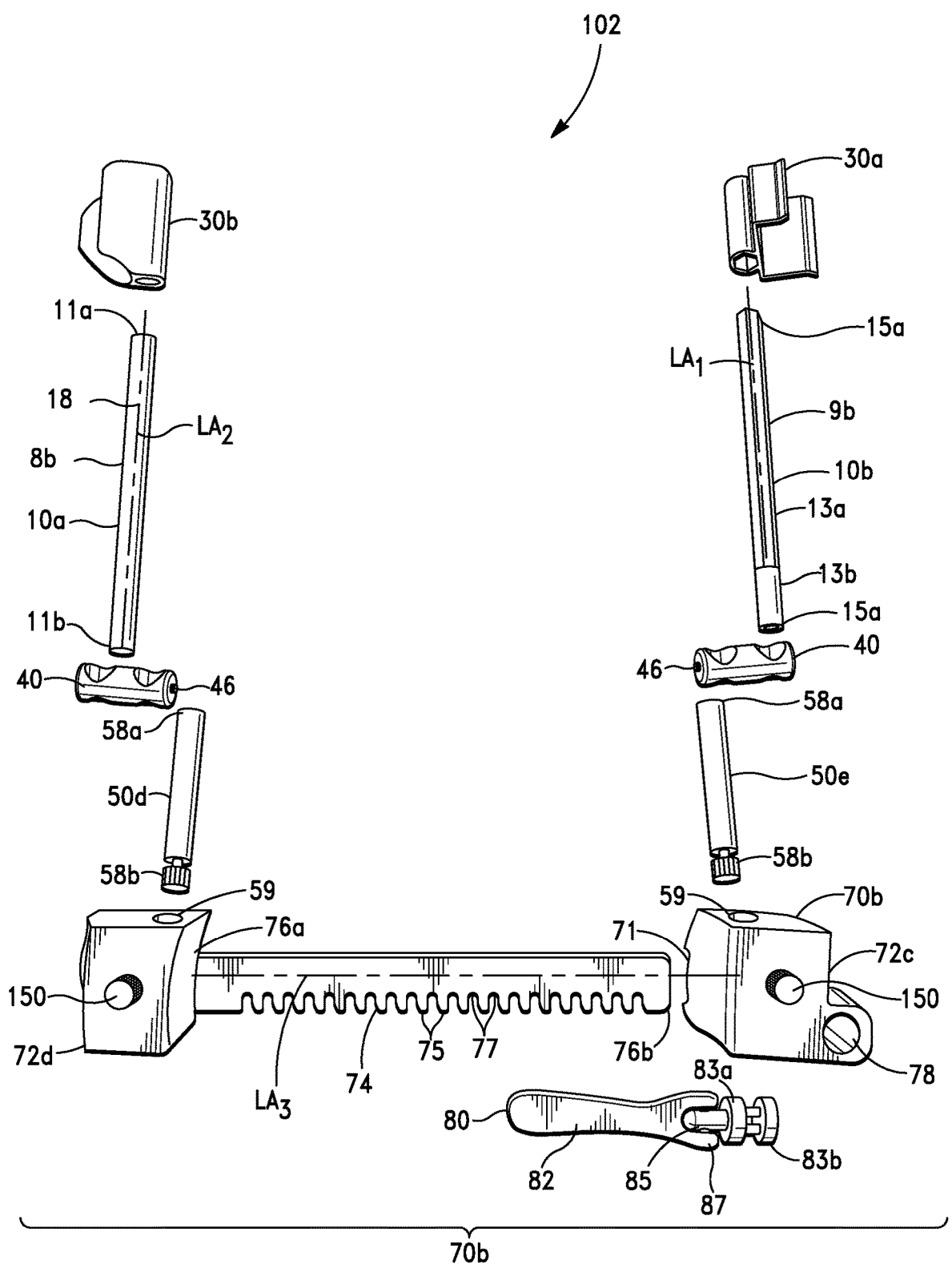
FIG. 11A is an exploded view of another embodiment of a thoracic structure access system, in accordance with the invention.
Figure 11B:
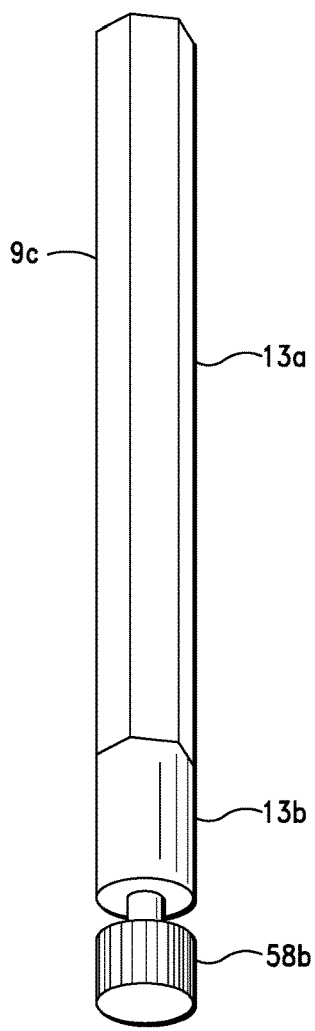
FIG. 11B is a perspective view of another embodiment of a tissue retractor arm, in accordance with the invention.
Figure 11C:
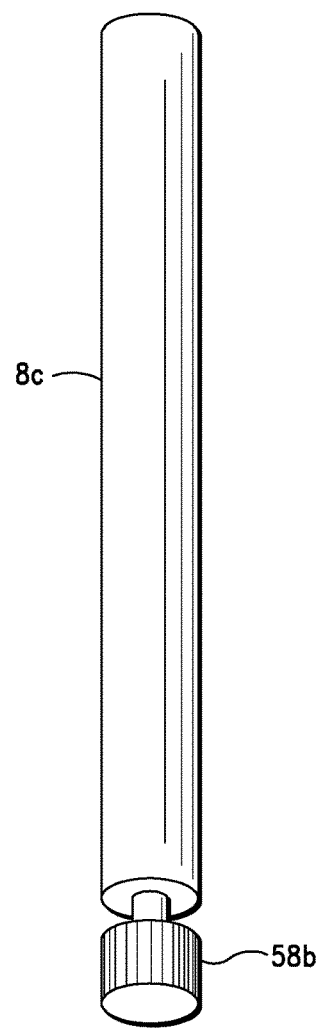
FIG. 11C is a perspective view of another embodiment of a tissue retention arm, in accordance with the invention.

In a preferred embodiment, the coupling member receiving channel 66 is also sized and configured to slidably directly receive the distal end of an elongated member of a tissue retractor or retention arm of the invention, i.e., elongated members 10a and 10b, and/or a tissue retractor or retention arm, such as the tissue arms 9c and 8c shown in FIGS. 11B and 11C, therein.

As additionally illustrated in FIGS. 6A-6C, in a preferred embodiment, the base members 60 further comprise the aforementioned base member arm/coupling member retention system. In a preferred embodiment, the arm/coupling member retention system comprises (i) first retention means (denoted "65a" and shown in phantom), which is configured and adapted to cooperate with the arm assemblies and coupling members of the invention, in this instance, coupling members 50a and 50b, when in communication therewith to secure the coupling members 50a and 50b (and arm assemblies and members, if directly connected to the base members 60) at a desired position (or positions) in the coupling member receiving channels 66 of the base members 60, and (ii) second retention means (denoted "65b" and also shown in phantom), which is configured and adapted to secure the base member retention rods 73a, 73b of the first and second ratchet sub-assemblies 72a, 72b in the base member retention rod channel 64.

According to the invention, various conventional retention means can be employed to secure the coupling members (and arm assemblies) of the invention, e.g., coupling members 50a and 50b, in the coupling member receiving channel 66 and base member retention rods 73a, 73b of the first and second ratchet sub-assemblies 72a, 72b in the base member retention rod channel 64.

In a preferred embodiment, the base member first and second retention means 65a, 65b comprise a conventional spring-loaded shaft system.

As illustrated in FIGS. 6B and 6C, to accommodate the conventional spring-loaded shaft system, the base member 60 further comprises retention means holes or lumens 67 that are sized and configured to receive and cooperate with the spring-loaded shaft system, i.e., first and second retention means 65a, 65b.

In some embodiments, the first and second retention means 65a, 65B are further configured and adapted to cooperate with the arm assemblies and coupling members of the invention, in this instance, coupling members 50a and 50b, when in communication therewith to fix the coupling members 50a and 50b (and arm assemblies and members, if directly connected to the base members 60) at a desired position (or positions) and abate rotation of the coupling members 50a and 50b.

As illustrated in FIGS. 2A and 2C, in a preferred embodiment, the proximal end 55a of the coupling member 50b is sized and configured to slidably translate into a receiving channel 44b of the interconnector member 40 to facilitate rotation of the interconnector member 40 and, thereby, the aforementioned rotation of the elongated arm member 10a when the elongated arm member 10a is operatively connected to the interconnector member 40.

Referring now to FIGS. 2A and 2B, in the illustrated embodiment, the retention arm assembly 8a comprises an elongated arm member 10b and a coupling member 50a, which is engaged to (preferably releasably engaged to) the elongated arm member 10b and directly releasably engaged to base member 60.

In some embodiments of the invention, the retention arm assembly 8a also comprises an interconnector member, such as interconnector member 40 shown in FIG. 3A, and a coupling member (i.e., a structure similar to retractor arm assembly 9a).

In the noted embodiments, the interconnector member is similarly configured and adapted to slidably receive the distal end of the elongated arm member 10b and the proximal end of the coupling member therein to similarly facilitate rotation of the elongated arm member 10b in a substantially perpendicular plane relative to the longitudinal axis (denoted "LA₁") when the elongated arm member 10b is operatively connected to the interconnector member.

The interconnector member can also similarly comprise a structure that additionally facilitates angular articulation of the elongated arm member 10b relative to its longitudinal axis "LA₁", i.e., facilitates spreading of the proximal end 15a of the elongated arm member 10b relative to its longitudinal axis "LA₁".

Figure 7:
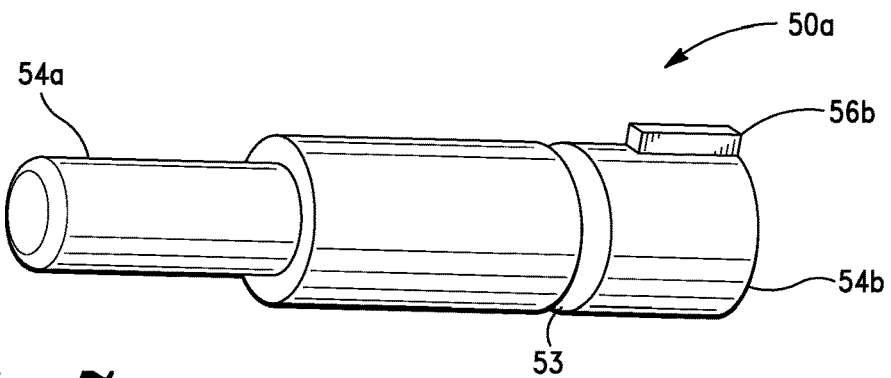
FIG. 7 is a perspective view of the retention arm coupling member of the tissue retention arm assembly shown in FIGS. 2A and 2B, in accordance with the invention.

Referring now to FIG. 7, the coupling member 50a of the retention arm assembly 8a comprises a cylindrical member comprising proximal engagement end region or end 54a and a distal end 54b. As illustrated in FIG. 7, the coupling member 50a similarly comprises a retainer ring or circumferential groove 53 disposed proximate the distal end 54b that is sized and configured to receive and cooperate with the arm/coupling member retention system; particularly, first retention means 65a of the base members 60.

As further illustrated in FIG. 7, the distal end 54b of the coupling member 50a similarly comprises locking tooth 56b that is configured to prevent unwanted rotation of the coupling member 50a when engaged to the base member 60, as shown in FIG. 2B.

Figure 8A:
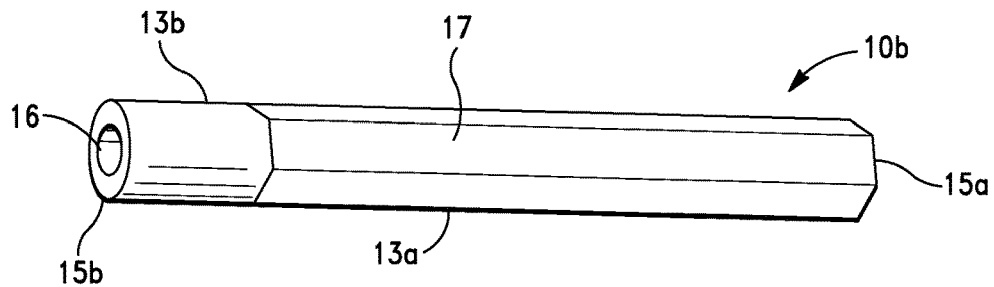
FIG. 8A is a perspective view of the elongated arm member of the tissue retention arm assembly shown in FIGS. 2A and 2B, in accordance with the invention.

Referring now to FIG. 8A, in a preferred embodiment, the elongated arm member 10b comprises a rod structure comprising a first body region 13a comprising a hexagonal shaped cross-section and a second body region 13b disposed proximate the distal end 15b of the elongated arm member 10b comprising a cylindrical shaped cross section.

As illustrated in FIG. 8A, the elongated arm member 10b further comprises a coupling member channel 16 disposed on the cylindrical distal end 15b, which is sized and configured to slidably receive and engage the proximal engagement end region or end 54a of coupling member 50a.

In some embodiments, the proximal engagement end region or end 54a of coupling member 50a comprises a textured feature on at least a portion of the exterior surface of the proximal engagement end region or end 54a to reduce the risk of accidental dislodgment of the coupling member 50a from the elongated arm member 10b. According to the invention, suitable textured features similarly include, but are not limited to, grooves and ribs.

Figure 8B:
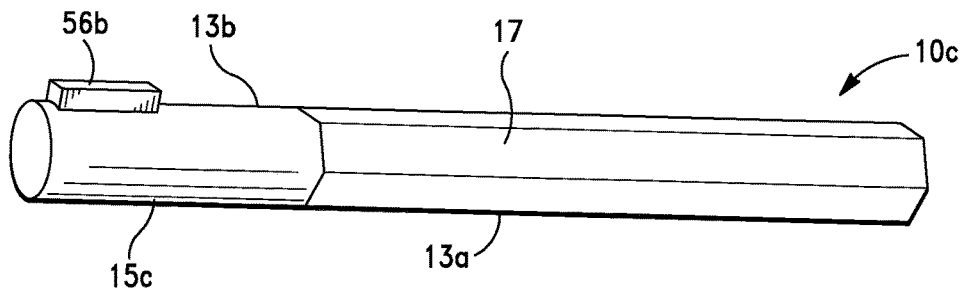
FIG. 8B is a perspective view of another embodiment of a retention arm, in accordance with the invention.

Referring now to FIG. 8B, there is shown a further embodiment of elongated arm member 10b (now denoted "10c"). As illustrated in FIG. 8B, the elongated arm member 10c comprises an elongated second body region 13b with locking tooth 56b disposed thereon. According to the invention, the distal end 15c of the elongated arm member 10c is sized and configured to directly slide into and, hence, be received by the coupling member receiving channel 66 of the base member 60, and, hence, eliminate the need for the coupling member 50a.

As further illustrated in FIGS. 2A and 2B, the elongated arm member 10b further comprises a tissue retractor member 30a (referred to in priority U.S. provisional Pat. App. No. 63/199,780 as "surgical retractor blades" and "blades"), which is configured and adapted to receive and slidably translate over the elongated arm member 10b.

In a preferred embodiment, the tissue retractor member 30a is similarly sized, configured and adapted to releasably engage and retain biological tissue proximate a xiphoid incision 6 at a transxiphoid incision site 7 during spreading and lifting of the lower portion 4 of the sternum 200, i.e., providing a thoracic opening or void, with the thoracic structure access system 100.

Figure 9:
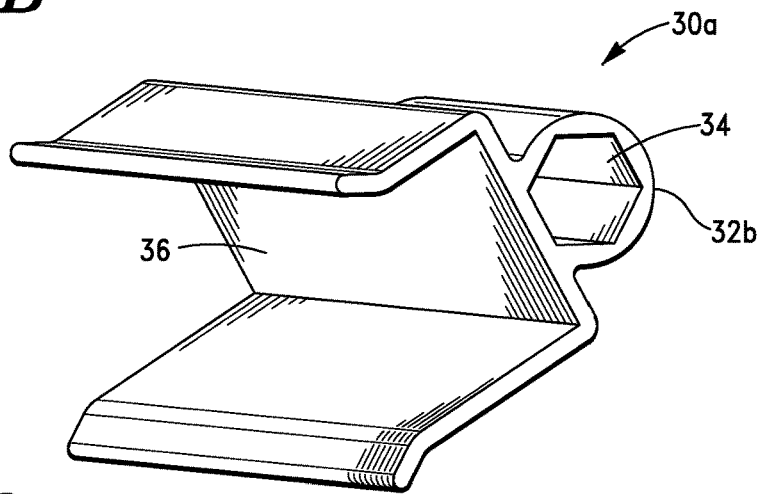
FIG. 9 is a perspective view of the tissue retractor member of the tissue retention arm assembly shown in FIGS. 2A and 2B that is also configured to engage biological tissue, in accordance with the invention.

Referring now to FIG. 9, the tissue retractor member 30a preferably comprises an elongated arm member engagement end 32b comprising an arm member receiving channel or opening 34 that is sized and configured to receive the first hexagonal shaped body region 13a of elongated arm member 10b, and a tissue engaging recess 36 that is sized and configured to receive and retain biological tissue therein.

As illustrated in FIG. 9, the arm member receiving opening 34 of the tissue retractor member 30a comprises a substantially hexagonal shape that preferably corresponds to the first hexagonal shaped body region 13a of elongated arm member 10b, whereby, when the tissue retractor member 30a is positioned on region 13a of the elongated arm member 10b, rotation of the tissue retractor member 30a is abated.

According to the invention, the tissue retractor member 30a can comprise any suitable configuration and/or size to releasably engage and retain various biological tissue sizes and dimensions.

According to the invention, the retention arm assembly 8a can also comprise any number of tissue retractor members 30a. In some embodiments, the retention arm assembly 8a comprises a plurality of tissue retractor members 30a. In a preferred embodiment, the retention arm assembly 8a comprises one (1) tissue retractor member 30a, as shown in FIGS. 2A and 2B.

According to the invention, the tissue retractor member(s) 30a can similarly be positioned at any suitable point along the length of the elongated arm member 10b.

According to the invention, the elongated arm members 10a, 10b and coupling members 50a, 50b, 50c (and coupling members 50d, 50e shown in FIG. 11A) of the invention can comprise various metals, including without limitation, stainless steel, titanium, tantalum and alloys thereof.

The elongated arm members 10a, 10b and coupling members 50a, 50b, 50c (and coupling members 50d, 50e discussed below) of the invention can also comprise various polymers, including, without limitation, polyethylene (PE), polypropylene (PP), polyethylene terephthalate (PET), polyimide (PA), polyvinyl chloride (PVC), acrylonitrile butadiene (ABS), polyetheretherketone (PEEK), polyaryletherketone (PAEK), polyurethane (PU), acrylic, polycarbonate (PC), polyacrylamide (PARA), polyphenylsulfone (PPS), and like polymeric materials.

In a preferred embodiment, the elongated arm members 10a, 10b and coupling members 50a, 50b, 50c (and coupling members 50d, 50e) of the invention comprise medical surgical steel, such as 316l stainless steel and 400 series stainless steels, or titanium.

According to the invention, the retractor arm sub-assemblies 20 and tissue retractor member 30a (and tissue retractor member 30b, discussed below) of the invention can similarly comprise various metals, including, without limitation, one of the aforementioned metals.

The retractor arm sub-assemblies 20 and tissue retractor members 30a, 30b of the invention can also comprise various polymers, including, without limitation, one of the aforementioned polymers.

In some embodiments, the retractor arm sub-assemblies 20 and tissue retractor members 30a, 30b of the invention comprise PEEK.

As indicated above, the thoracic structure access systems of the invention, i.e., thoracic structure access system 100 and thoracic structure access system 102, discussed below, comprise modular systems, whereby the arm assemblies and coupling members of the invention, i.e., retractor arm assembly 9a, retention arm assembly 8b and coupling members 50a, 50b, are interchangeable. The arm assemblies and coupling members of the invention can thus be employed on different sides of the arm assembly transverse motion inducing means of the invention, discussed below.

The retractor arm sub-assemblies 20 and tissue retractor members 30a, 30b of the invention can thus similarly be deployed on either the retractor arm assembly 9a or retention arm assembly 8b of the invention.

Referring back to FIG. 2A, in a preferred embodiment, the base member 60 of retractor arm assembly 9a is operatively connected to arm assembly transverse motion inducing means, which, as discussed in detail below, is configured and adapted to provide lateral movement of the retractor arm assembly 9a relative to its longitudinal axis (denoted "LA$_2$").

As illustrated in FIG. 2A, in a preferred embodiment, the arm assembly transverse motion inducing means comprises a ratchet assembly 70a. As further illustrated in FIG. 2A, the ratchet assembly 70a comprises a longitudinal axis (denoted "LA$_3$").

Figure 10A:
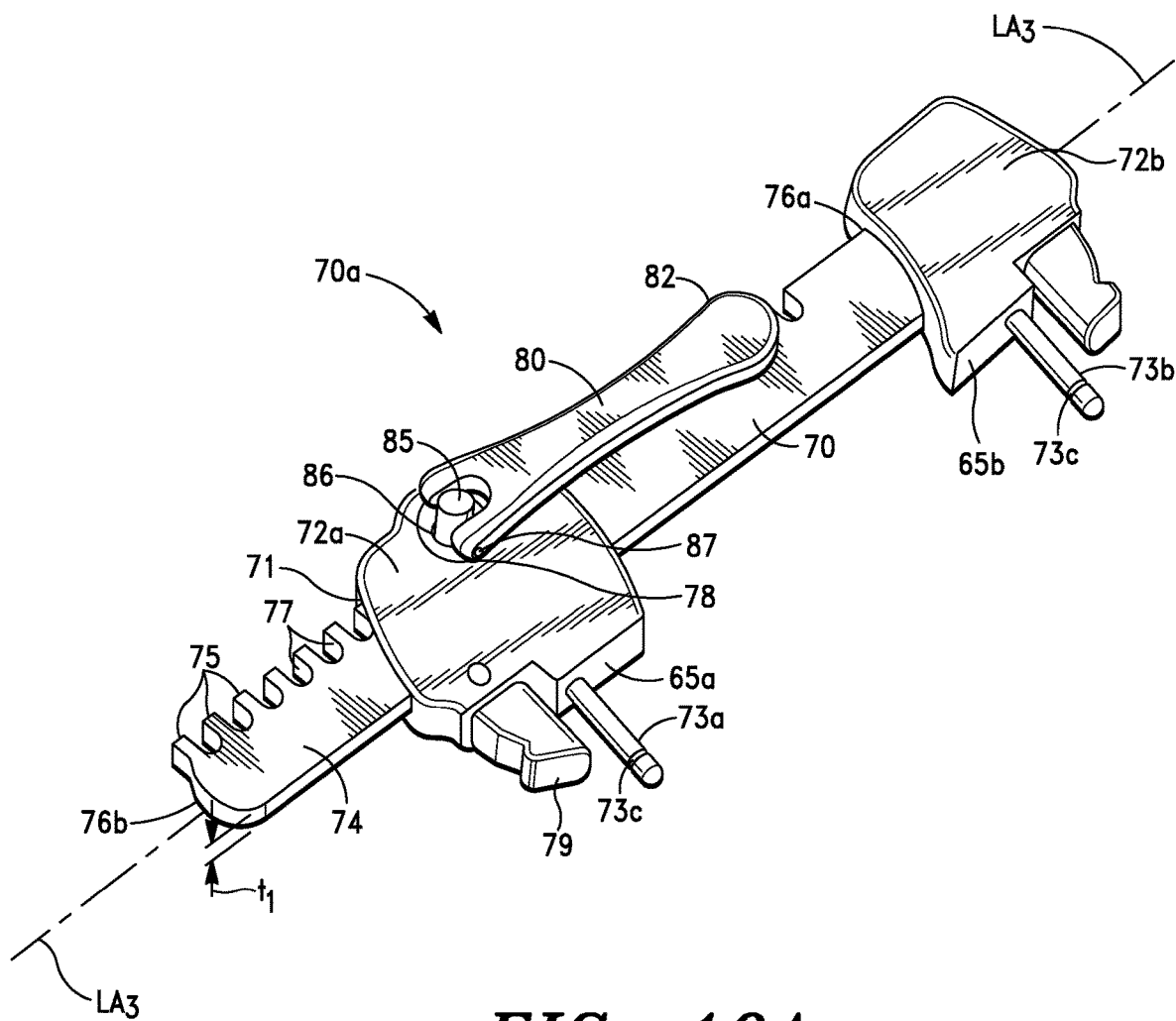
FIG. 10A is a perspective view of the ratchet assembly of the thoracic structure access system shown in FIG. 2A, in accordance with the invention.
Figure 10B:
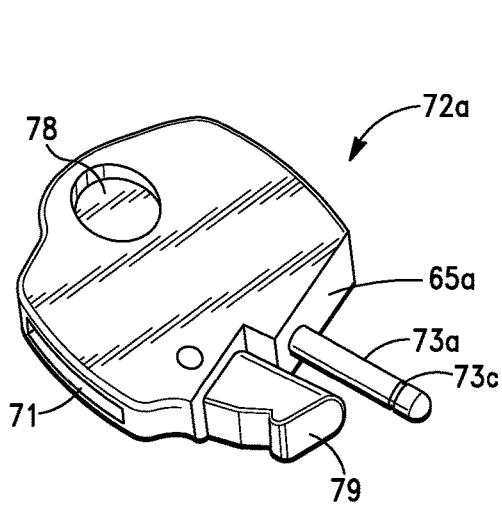
FIG. 10B is a perspective view of a ratchet sub-assembly of the ratchet assembly shown in FIG. 10A, in accordance with the invention.
Figure 10C:
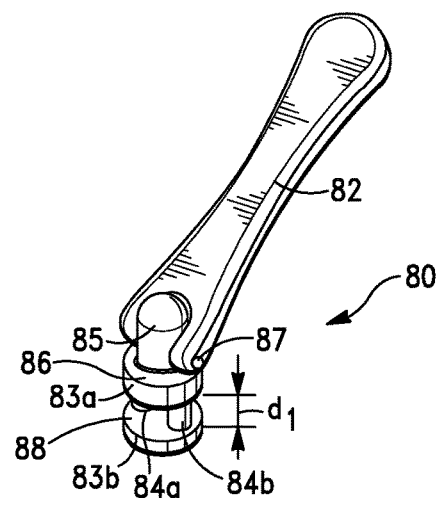
FIG. 10C is a perspective view of the ratchet handle assembly of the ratchet assembly shown in FIG. 10A, in accordance with the invention.

Referring now to FIGS. 10A, 10B and 10C, there is shown one embodiment of a ratchet assembly 70a that is that is configured and adapted to provide lateral movement of the retractor arm assembly 9a relative to its longitudinal axis "LA$_2$" (i.e., lateral movement parallel to the longitudinal axis "LA$_3$" of the ratchet assembly 70a).

As illustrated in FIGS. 10A and 10B, the ratchet assembly 70a comprises a toothed crossbar 74 comprising proximal and distal ends 76a, 76b, and a plurality of teeth 75 having gaps 77 disposed therebetween. The ratchet assembly 70a further comprises first and second ratchet sub-assemblies 72a, 72b that are mounted on the toothed crossbar 74.

As additionally illustrated in FIGS. 10A and 10B, the second ratchet sub-assembly 72b is statically mounted to the proximal end 76a of the toothed crossbar 74 and the first ratchet sub-assembly 72a is slidably engaged to the toothed crossbar 74 and, as discussed below, is configured to laterally translate along the toothed crossbar 74.

According to the invention, the first ratchet sub-assembly 72a is preferably laterally translated along the toothed crossbar 74 using a pair of first and second drive pins 84a, 84b of handle assembly 80, which are positioned and configured to releasably and sequentially engage gaps 77 of the toothed crossbar 74 in a cogging manner.

As illustrated in FIG. 10C, the handle assembly 80 comprises a drive handle 82 that is operatively engaged to first and second cylindrical drive bearings 83a, 83b. First cylindrical drive bearing 83a preferably comprises a raised boss 85 extending from a drive bearing surface 86 to which drive handle 82 is operatively connected, preferably, pivotally connected, by way of pin 87.

As further illustrated in FIG. 10C, second cylindrical drive bearing 83b comprises first and second drive pins 84a, 84b, which extend toward the first drive bearing 83a from a surface 88 thereof and terminate at first drive bearing 83a. The first and second drive bearings 83a, 83b are preferably spaced apart a pre-determined distance (denoted di), which is preferably slightly greater than the thickness (denoted ti) of the toothed crossbar 74, such that a portion of the crossbar 74 can be received between drive bearings 83a, 83b.

Referring to FIG. 10B, in a preferred embodiment, the first and second drive bearings 83a, 83b are sized and configured to rotatably seat in the guide hole 78 of first ratchet sub-assembly 72a.

As illustrated in FIG. 10B, first ratchet sub-assembly 72a comprises a slot or opening 71 extending therethrough that is sized and configured to slidably receive the toothed crossbar 74. Preferably, slot 71 comprises a shape that corresponds to the shape and dimensions of the cross-section of at least the distal end 76b of the crossbar 74.

In a preferred embodiment, when the handle assembly 80 is seated in guide hole 78 of the first ratchet sub-assembly 72a, the handle assembly 80 is preferably in communication with the crossbar 74 when the distal end 76b of crossbar 74 is in slot 71, whereby, when the drive handle 82 is rotated in first and second directions, the first and second drive pins 84a, 84b releasably, sequentially engage the gaps 77 between teeth 75 and lateral motion of the first ratchet sub-assembly 72a in either direction along (or parallel to) the longitudinal axis LA₃ of the crossbar 74 is provided.

As further illustrated in FIGS. 10A and 10B, in a preferred embodiment, first ratchet sub-assembly 72a comprises a brake mechanism 79 that is configured to abut the toothed crossbar 74 and lock the first ratchet sub-assembly 72a at a pre-determined position along the crossbar 74.

As additionally illustrated in FIGS. 10A and 10B, first and second ratchet sub-assemblies 72a, 72b further comprise base member retention rods 73a, 73b that are sized and configured to press-fit (or interference fit) into the base member retention rod channel 64 of base member(s) 60, whereby the bottom surface 64a of base member(s) 60 is allowed to abut receiving surfaces 65a, 65b of the first and second ratchet sub-assemblies 72a, 72b.

In a preferred embodiment, the base member retention rods 73a, 73b similarly comprise a retainer ring or circumferential groove 73c disposed proximate the distal end of the base member retention rods 73a, 73b that is sized and configured to receive and cooperate with the first retention means 65a of the base members 60 to prevent unwanted withdrawal of the base member retention rods 73a, 73b from the base member 60.

In some embodiments of the invention, the bottom surface 64a of base member(s) 60 comprise anti-rotation means, such as surface features or adherence means, to abate movement, e.g., rotation, of base members 60 relative to the first and second ratchet sub-assemblies 72a, 72b.

As illustrated in FIG. 2A, in at least one embodiment, the base members 60 abut brake mechanism 79, which also abates unwanted movement of base members 60 relative to the first and second ratchet sub-assemblies 72a, 72b.

As further illustrated in FIG. 2A, in a preferred embodiment, base member retention rods 73a, 73b are press-fit into the base member retention rod channel 64 of base members 60 to engage (preferably releasably engage) retractor arm assembly 9a to the first ratchet sub-assembly 72a and retention arm assembly 8a to the second ratchet sub-assembly 72b.

According to the invention, the ratchet assembly 70a can comprise more than one movable ratchet sub-assembly 72a. In some embodiments, the ratchet assembly 70a comprises two movable ratchet sub-assemblies.

According to the invention, the retractor arm assembly 9a and retention arm assembly 8a can comprise coupling members 50d and 50e, discussed below, which are sized and configured to releasably engage alternative embodiments of ratchet sub-assemblies 72a, 72b, such as ratchet sub-assemblies 72c, 72d of ratchet assembly 70b shown in FIG. 11A, directly.

Referring now to FIG. 11A, there is shown another embodiment of thoracic structure access system of the invention (denoted "102").

As illustrated in FIG. 11A, the thoracic structure access system 102 also comprises a modular structure similar thoracic structure access system 100, i.e., a pair of arm assemblies and at least one arm assembly transverse motion inducing means.

However, as discussed in detail below, in this embodiment, the thoracic structure access system 102 comprises further embodiments of retention and retractor arm assemblies.

In some embodiments, the retention arm assembly of the thoracic structure access system 102 (now denoted "8b") similarly comprises elongated arm member 10a. However, as shown in FIG. 11A, in the illustrated embodiment, the retention arm assembly 8b further includes interconnector member 40, discussed above, and a coupling member 50d.

As illustrated in FIG. 11A, in a preferred embodiment, the elongated arm member 10a is similarly releasably engaged to the interconnector member 40, which similarly facilitates rotation of the elongated arm member 10a in a substantially perpendicular plane relative to its longitudinal axis "LA₂" when the elongated arm member 10a is operatively connected to the interconnector member 40, and, as discussed below, the coupling member 50d is engaged to the second ratchet sub-assembly 72d of ratchet assembly 70b and also connected to the interconnector member 40.

Figure 12:
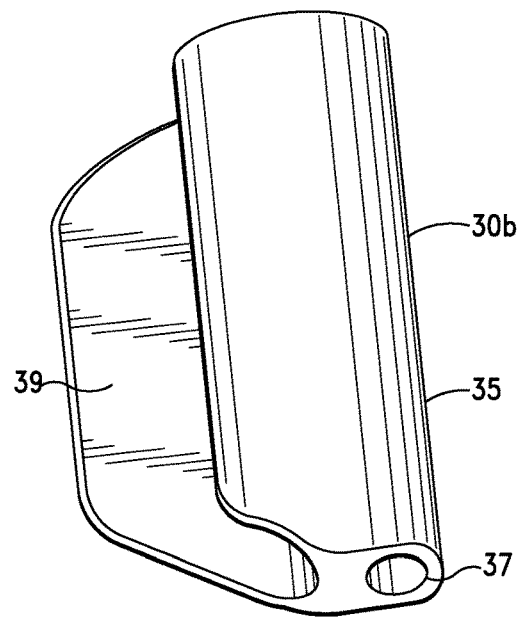
FIG. 12 is a perspective view of another embodiment of a tissue retractor member that is configured to engage biological tissue, in accordance with the invention.

As further illustrated in FIGS. 11A and 12, the elongated arm member 10a further comprises another embodiment of a tissue retractor member of the invention (denoted "30b") that is releasably engaged to the elongated arm member 10a.

According to the invention, the tissue retractor member 30b is similarly sized, configured and adapted to releasably engage and retain biological tissue proximate a xiphoid incision 6 at a transxiphoid incision site 7 during spreading and lifting of the lower portion 4 of the sternum 200, i.e., providing a thoracic opening or void, with the thoracic structure access system 102.

As illustrated in FIG. 12, the tissue retractor member 30b comprises an elongated arm member engagement end 35 comprising an arm member receiving channel or opening 37 that is sized and configured to receive the elongated arm member 10a therethrough, and a tissue engaging recess 39 that is sized and configured to receive and retain biological tissue therein.

In some embodiments, the elongated arm member 10a similarly comprises textured features on at least a portion of the exterior surface 18 to abate movement, e.g., rotation, of the tissue retractor member 30b when positioned on the elongated arm member 10a.

According to the invention, the retention arm assembly 8b can similarly comprise any number of tissue retractor members 30b. In some embodiments, the retention arm assembly 8b comprises a plurality of tissue retractor members 30b. In a preferred embodiment, the retention arm assembly 8b comprises one (1) tissue retractor member 30b, as shown in FIG. 11A.

According to the invention, the tissue retractor member(s) 30b can similarly be positioned at any suitable point along the length of the elongated arm member 10a.

As further illustrated in FIG. 11A, the retention arm assembly 8b is releasably engaged to the ratchet assembly 70b via a coupling member 50d. The coupling member 50d comprises a proximal end 58a that is sized and configured to slidably translate into a receiving channel, i.e., receiving channel 44a or 44b, of the interconnector member 40 to similarly facilitate rotation of the interconnector member 40 and, thereby, the aforementioned rotation of the elongated arm member 10a when the elongated arm member 10a is operatively connected to the interconnector member 40.

In a preferred embodiment, the coupling member 50d further comprises a gear-tipped distal end 58b that is sized and configured to be received in and releasably engage coupling member channels 59 of first and second ratchet sub-assemblies 72c, 72d of ratchet assembly 70b.

As illustrated in FIG. 11A, in this embodiment, the retractor arm assembly 9b of the thoracic structure access system 102 now comprises elongated arm member 10b. As further illustrated in FIG. 11A, the retractor arm assembly 9b further comprises interconnector member 40 and a coupling member 50e.

In a preferred embodiment, the elongated arm member 10b is similarly releasably engaged to the interconnector member 40, which similarly facilitates rotation of the elongated arm member 10b in a substantially perpendicular plane relative to its longitudinal axis "$LA_1$" when the elongated arm member 10b is operatively connected to the interconnector member 40, and, as discussed below, the coupling member 50e is engaged to the first ratchet sub-assembly 72c of ratchet assembly 70b and also connected to the interconnector member 40.

As further illustrated in FIG. 11A, the elongated arm member 10b further comprises tissue retractor member 30a, which, as indicated above, is similarly (i) configured and adapted to receive and slidably translate over the first hexagonal shaped body region 13a of elongated arm member 10b and (ii) sized, configured and adapted to releasably engage and retain biological tissue proximate a xiphoid incision 6 at a transxiphoid incision site 7 during spreading and lifting of the lower portion 4 of the sternum 200, i.e., providing a thoracic opening or void, with the thoracic structure access systems of the invention.

According to the invention, the retractor arm assembly 9b can similarly comprise any number of tissue retractor members 30a. In a preferred embodiment, the retractor arm assembly 9b comprises one (1) tissue retractor member 30a.

According to the invention, the tissue retractor member(s) 30a can also be positioned at any suitable point along the length of the elongated arm member 10b.

As further illustrated in FIG. 11A, the retractor arm assembly 9b is preferably releasably engaged to ratchet assembly 70b via a coupling member 50e. The coupling member 50e similarly comprises a proximal end 58a that is sized and configured to slidably translate into a receiving channel of the interconnector member 40, e.g., receiving channel 44b, to facilitate rotation of the interconnector member 40 and, thereby, the aforementioned rotation of the elongated arm member 10b when operatively connected thereto.

In a preferred embodiment, the coupling member 50e also comprises a gear-tipped distal end 58b that is sized and configured to be received in and releasably engage coupling member channels 59 of first and second ratchet sub-assemblies 72c, 72d of ratchet assembly 70b.

Referring now to FIGS. 11B and 11C, in some embodiments of the invention, the thoracic structure access system 102 comprises retractor arm assembly 9c and retention arm assembly 8c. As illustrated in FIGS. 11B and 11C, the retractor arm assembly 9c and retention arm assembly 8c comprise an elongated single structure that similarly comprises the gear-tipped distal end 58b, which is sized and configured to be received in and releasably engage coupling member channels 59 of first and second ratchet sub-assemblies 72c, 72d of ratchet assembly 70b. The retractor arm assembly 9c and retention arm assembly 8c are thus configured to directly engage first and second ratchet sub-assemblies 72c, 72d of ratchet assembly 70b and, hence, eliminate the need for coupling members 50d, 50e.

As indicated above, the thoracic structure access system 102 of the invention similarly comprises a modular system, whereby the arm assemblies and coupling members of the invention, i.e., retractor arm assemblies 9b, 9c, retention arm assemblies 8b, 8c and/or coupling members 50d, 50e, are interchangeable. The arm assemblies and coupling members of the invention can thus similarly be employed on different sides of the arm assembly transverse motion inducing means of the invention, discussed below.

The tissue retractor members 30a, 30b of the invention can thus similarly be deployed on either the retractor arm assembly 9b or 9c or retention arm assembly 8b or 8c of the invention.

As illustrated in FIG. 11A, the thoracic structure access system 102 further comprises another embodiment of a ratchet assembly of the invention (denoted "70b").

As further illustrated in FIG. 11A, the ratchet assembly 70b similarly comprises toothed crossbar 74 described above (or a similar crossbar member). However, in this embodiment, the ratchet assembly 70b comprises further embodiments of ratchet sub-assemblies, i.e., first and second ratchet sub-assemblies 72c, 72d, which, as shown in FIG. 11A, are similarly configured and adapted to be mounted on toothed crossbar 74.

In a preferred embodiment, the first ratchet sub-assembly 72c and, thereby, retractor arm assembly 9b (and retractor arm assembly 9c, if employed), is similarly configured and adapted to laterally translate along the toothed crossbar 74 in substantially the same manner as first ratchet sub-assembly 72a.

In a preferred embodiment, the second ratchet sub-assembly 72d and, thereby, retention arm assembly 8b (and retention arm assembly 8c, if employed), is statically mounted to the proximal end 76a of the toothed crossbar 74.

In some envisioned embodiments of the invention, the thoracic structure access system 102 comprises two of the first ratchet sub-assembly 72c; one first ratchet sub-assembly 72c being operatively connected to retractor arm assembly 9b (or retractor arm assembly 9c, if employed) to provide lateral motion of the retractor arm assembly 9b (and retractor arm assembly 9c) along (or parallel to) the toothed crossbar 74 and the other first ratchet sub-assembly 72c being operatively connected to retention arm assembly 8b (or retention arm assembly 8c, if employed) to similarly provide lateral motion of the retention arm assembly 9b (and retention arm assembly 8c) along (or parallel to) the toothed crossbar 74.

In such embodiments, retention arm assembly 8b would accordingly comprise a second retraction arm assembly.

As further illustrated in FIG. 11A, the first and second ratchet sub-assemblies 72c, 72d preferably comprise pinions 150 that are configured to operatively engage with the gear-tipped distal ends 58b of coupling members 50d, 50e (and retractor and retention arm assemblies 9c and 8c, if employed) when releasably engaged to ratchet sub-assemblies 72d, 72c, respectively.

In a preferred embodiment, the pinions 150 are configured and adapted to rotate the retention and retractor arm assemblies 8b, 9b (and retractor and retention arm assemblies 9c and 8c, if employed) in substantially perpendicular planes relative to the longitudinal axes of the elongated arm members when the arm members are in communication with, i.e., operatively connected to, the pinions 150.

In some embodiments, the pinions 150 are manually actuated. In some embodiments, pinions 150 are electronically, e.g., computer, actuated. In some embodiments, the pinions 150 are actuated by a remotely controlled surgical system, e.g., a daVinci® Surgical System.

In some embodiments, the pinions 150 comprise a knurled head to accommodate actuation by a surgeon.

In some embodiments, the pinions 150 are configured and adapted to operatively connect to and, hence, cooperate with a pinion actuation tool.

In some embodiments, the first and second ratchet sub-assemblies 72c, 72d are further configured and adapted to induce angular articulation of coupling members 50d, 50e and, thereby, retention and retractor arm assemblies 8b, 9b relative to the longitudinal axes $LA_2$ and $LA_1$ of the elongated arm members 10a, 10b when the coupling members 50d, 50e are operatively connected to the first and second ratchet sub-assemblies 72c, 72d.

In some embodiments, the first and second ratchet sub-assemblies 72c, 72d are similarly configured and adapted to induce the noted angular articulation of retractor and retention arm assemblies 9c and 8c, when employed.

According to the invention, ratchet assembly 70b can also be employed with thoracic structure access system 100.

As indicated above, the thoracic structure access systems of the invention (i.e., thoracic structure access systems 100, 102) are configured to retract biological tissue and provide access to internal biological structures; particularly, intrathoracic structures, e.g., the heart and internal mammary arteries, to facilitate entry through the biological tissue with surgical instruments and interaction of the surgical instruments with the intrathoracic structures during a thoracic surgical procedure; particularly, a minimally invasive CAGB and/or OPCAB procedure.

A minimally invasive CABG or OPCAB procedure employing the thoracic structure access systems (and associated apparatus) of the invention will now be described in detail.

As indicated above, it is, however, to be understood that, although operation of the thoracic structure access systems of the invention is described and illustrated in connection with a minimally invasive CABG procedure; particularly, a MINI OPCAB procedure, the thoracic structure access systems and apparatus of the invention are not limited to such procedures. Indeed, as indicated above, the thoracic structure access systems (and associated apparatus) of the invention can also be readily employed to provide access to intrathoracic biological tissue structures of a subject; particularly, access via a xiphoid incision, in conjunction with other surgical procedures, e.g., heart valve replacement.

According to the invention, the first step in performing a minimally invasive CAGB (and/or OPCAB) procedure is to provide, assemble and prepare a thoracic structure access system of the invention, in this instance, thoracic structure access system 100, for the procedure (denoted method step "i").

According to the invention, the seminal components of the thoracic structure access systems of the invention can be assembled in any suitable order. Referring again to FIGS. 2A and 2B, in a preferred embodiment, the thoracic structure access system 100 is assembled as follows:

(a) coupling member 50a is releasably engaged to elongated arm member 10b and a base member 60, as described above;

(b) coupling member 50b is releasably engaged to interconnector member 40 and a base member 60, as described above;

(c) elongated arm member 10a is also releasably engaged to interconnector member 40, as described above;

(d) two (2) retractor arm sub-assemblies 20 are releasably engaged to elongated arm member 10a and tissue retractor member 30a is releasably engaged to elongated arm member 10b, as described above, to assemble retractor and retention arm assemblies 9a, 8a, respectively;

(e) in some embodiments of the invention, wherein the handle assembly 80 of the first ratchet assembly 70a is not an integral component of the first ratchet sub-assembly 72a, the handle assembly 80 is rotatably seated in guide hole 78 of the first ratchet sub-assembly 72a;

(f) the distal end 76b of toothed crossbar 74 is slidably translated into slot 71 of first ratchet sub-assembly 72a; and (g) retractor and retention arm assemblies 9a, 8a are then releasably engaged to first and second ratchet sub-assemblies 72a, 72b, respectively, as described above, to complete the assembly of thoracic structure access system 100.

After the retractor and retention arm assemblies 9a, 8a are engaged to first and second ratchet sub-assemblies 72a, 72b, the handle assembly 80 is actuated to laterally translate ratchet assembly 70a along the toothed crossbar 74 towards the second ratchet sub-assembly 72b, i.e., retractor and retention arm assemblies 9a, 8a are disposed proximate each other in preparation for use during the procedure.

According to the invention, the thoracic structure access system 100 can be modified to add, remove or interchange any suitable and compatible thoracic structure access system component. By way of example, additional retractor arm sub-assemblies 20 can be releasably engaged to or removed from elongated arm member 10a.

According to the invention, the thoracic structure access systems of the invention can also be configured to accept a myriad of conventional complementary surgical attachments including, without limitation, beating heart stabilizers, mist blowers, suction tubes, suction stabilizer tubes, suture retainment members or hooks, surgical lights and optical equipment, e.g., endoscopes.

In some embodiments, the elongated arm members of the invention, i.e., elongated arm members 10a, 10b are adapted and configured to releasably engage at least one conventional complementary surgical attachment.

Referring back to FIGS. 1A and 1B, after thoracic structure access system 100 is provided, assembled and prepared for use (denoted step "i"), a xiphoid incision 6 is made and, hence, provided at the transxiphoid incision site 7 (denoted step "ii").

In a preferred embodiment, the xiphoid incision 6 is made slightly above the xiphoid process 1 and the lower portion 4 of the sternum 200 and, preferably, substantially parallel with the longitudinal or craniocaudal axis of the subject 300 (denoted "$CA_1$").

According to the invention, the xiphoid incision 6 can comprise any suitable length and shape to provide an adequate working access space (and volume) for a surgeon. In a preferred embodiment, the xiphoid incision 6 comprises a length in the range of approximately 2-15 cm, more preferably, a length in the range of approximately 6-7 cm.

In a preferred embodiment, the transxiphoid incision site 7 extends from approximately 2-15 cm, more preferably, approximately 6-7 cm from below the distal end 2a of the xiphoid process 1 upwards towards subject's neck 3, as shown in FIG. 1A.

In some embodiments, transxiphoid incision site 7 is extended further downward below the distal end 2a of the xiphoid process 1.

After the xiphoid incision 6 is made in the sternum 200 (denoted step "ii"), a further incision is made in the pericardium of the subject's heart to accommodate insertion of surgical instruments commonly employed during a CABG (and/or OPCAB) procedure, such as an endoscope (denoted step "iii").

After the further incision is made in the pericardium (denoted step "iii"), in some embodiments, an endoscope is routed into and through the incision made in the pericardium to allow a surgeon to analyze and "inventory" the coronary arteries and internal mammary arteries to plan the CABG (and/or OPCAB) procedure based on the clinical status of the subject 300 (denoted step "iv"). By way of example, the noted analysis can include determining the distance between the internal mammary arteries (left and/or right) and the coronary arteries (left and/or right) to be bypassed to determine the necessary length of the internal mammary artery (also referred to as an internal thoracic artery) to be excised from the subject's vasculature for use as a vascular graft.

It is well established that visual inspection of a subject's coronary arteries and internal mammary arteries also reveals the functional and physical characteristics of the coronary and internal mammary arteries, e.g., the texture/color of the epicardium help to indicate the severity of the stenosis. Further, the position of the coronary arteries, including whether the target arteries are "intramyocardial" (below the surface of the epicardium), will indicate the access space (and volume) required at the surgical site and in the surgical field. At this juncture, the surgeon can confirm that the transxiphoid incision site 7 is appropriate for the CABG (and/or OPCAB) procedure.

Figure 13:
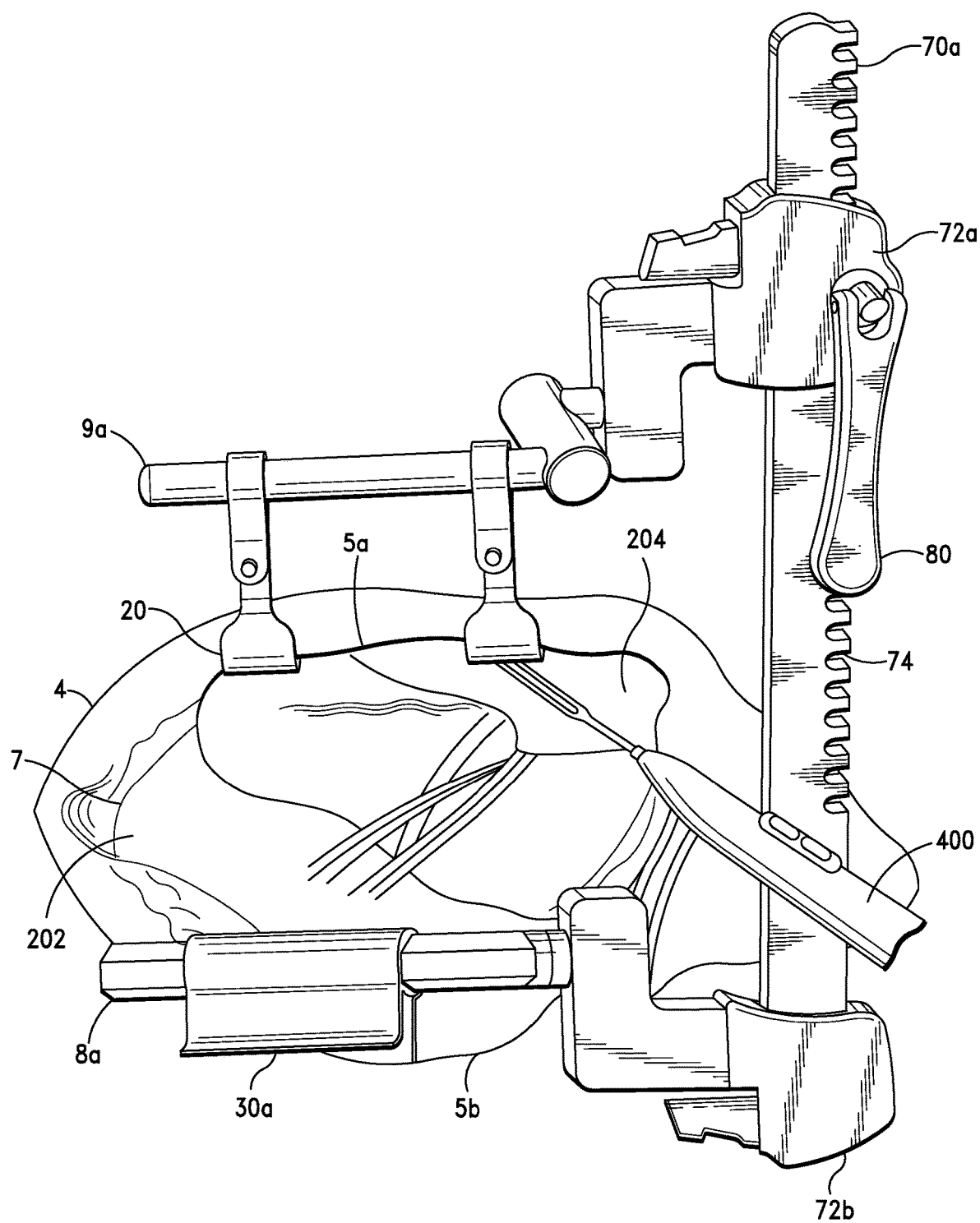
FIG. 13 is a front plan view of the thoracic tissue access system shown in FIG. 2A engaging biological tissue at a transxiphoid incision site to access intrathoracic structures, in accordance with the invention.

Referring now to FIG. 13, after the endoscope is routed into and through the incision made in the pericardium (denoted step "iv"), the thoracic structure access system 100 is positioned proximate the transxiphoid incision site 7 (denoted step "v").

After the thoracic structure access system 100 is positioned proximate the transxiphoid incision site 7 (denoted step "v"), the retention arm assembly 8a is positioned proximate first biological tissue proximate the transxiphoid incision site 7, i.e., thoracic tissue portion 5b, as shown in FIG. 13, in a manner such that a section of thoracic tissue portion 5b can be releasably engaged to tissue retractor member 30a (denoted step "vi").

After the retention arm assembly 8a is positioned proximate thoracic tissue portion 5b (denoted step "vi"), the retractor arm assembly 9a is positioned proximate opposed second biological tissue proximate the transxiphoid incision site 7, i.e., thoracic tissue portion 5a, as shown in FIG. 13, in a manner such that sections of thoracic tissue portion 5a can be releasably engaged to retractor arm sub-assemblies 20 (denoted step "vii").

After the retractor arm assembly 9a is positioned proximate thoracic tissue portion 5a (denoted step "vii"), the drive handle 82 of handle assembly 80 is actuated, i.e., rotated in a first direction, to laterally translate ratchet sub-assembly 72a along toothed crossbar 74 in a first pre-determined direction toward the distal end 76b of crossbar 74 with retractor arm assembly 9a operatively connected thereto, whereby the retention and retractor arm assemblies 8a, 9a spread and lift at least the lower portion 4 of the sternum 200 (by applying opposing forces to a section of thoracic tissue portion 5b and sections of thoracic tissue portion 5a and, thereby, offsetting thoracic tissue portion 5b and thoracic tissue portion 5a) to provide an access space 202 at the transxiphoid incision site 7 (denoted step "viii").

In some embodiments, ratchet sub-assembly 72a is locked at a pre-determined location along the toothed crossbar 74 to abate unwanted lateral movement of the ratchet sub-assembly 72a.

After the access space 202 is provided at the transxiphoid incision site 7 (denoted step "viii"), at least one internal mammary artery 204 (i.e., left or right internal mammary artery) is exposed, excised and processed for use as a coronary artery vascular graft for the CABG (or OPCAB) procedure (denoted step "ix").

According to the invention, the at least one internal mammary artery 204 can be excised and processed according to any conventional method. As further illustrated in FIG. 13, in some embodiments, the at least one internal mammary artery 204 is excised via a harmonic scalpel 400.

After at least one internal mammary artery 204 (i.e., left or right internal mammary artery) is exposed, excised and processed (denoted step "ix"), in some embodiments, a conventional beating heart stabilizer device, such as the beating heart stabilizer device disclosed in Applicants' U.S. Pat. No. 6,346,077, is releasably engaged to one of elongated arm members 10a, 10b (denoted step "x").

After a conventional beating heart stabilizer device is releasably engaged to one of elongated arm members 10a, 10b (denoted step "x"), the beating heart stabilizer device is employed to render a target coronary artery substantially motionless for coronary artery bypass, i.e., providing at least one anastomotic connection between the target coronary artery and a pre-determined vascular structure (denoted step "xi").

After a target coronary artery is rendered substantially motionless (denoted step "xi"), the anastomotic connections are then made between a target coronary artery and a pre-determined vascular structure, e.g., an in situ vascular graft from the left internal thoracic artery to the left anterior descending coronary artery (LITA to LAD) of a subject, while the beating heart stabilizer device is being employed to render the target coronary artery substantially motionless (denoted step "xii").

In some embodiments, after the anastomotic connections are then made between a target coronary artery and a pre-determined vascular structure (denoted step "xii"), another small incision is made in a subject's thorax just below the xiphoid process 1 and a drainage tube is routed from the pericardial space and through the small incision out of the subject's body (denoted step "xiii").

After the small incision is made below the xiphoid process and a drainage tube is routed from the pericardial space and through the small incision out of the subject's body (denoted step "xiii"), the endoscope is again employed to check the anastomotic connections for kinking or leaks, to check the position of the drainage tube, and to check the integrity of the pleural tissue (denoted step "xiv").

In some embodiments, a conventional flow probe is employed to check the patency of the anastomotic connections.

After the endoscope is employed to check the anastomotic connections for kinking or leaks, to check the position of the drainage tube, and to check the integrity of the pleural tissue (denoted step "xiv"), the drive handle 82 of handle assembly 80 is actuated, i.e. rotated in a second direction, to laterally translate ratchet sub-assembly 72a and, thereby retractor arm assembly 9a along toothed crossbar 74 in a second pre-determined direction toward the retractor sub-assembly 72b, whereby the force(s)/pressures(s) on the lower portion 4 of the sternum 200 (applied by the retractor arm and retention arm assemblies 9a, 8a on sections of thoracic tissue portion 5a and a section of thoracic tissue portion 5b, respectively) are relieved and to close access space 202 (denoted step "xv").

In some embodiments, wherein the ratchet sub-assembly 72a is locked to the toothed crossbar 74, the ratchet sub-assembly 72a is unlocked to allow lateral movement along the toothed crossbar 74 via handle assembly 80.

After the access space 202 is closed (denoted step "xv"), the drainage tube is routed out of the small incision provided in step "xiii", and the transxiphoid incision site 7 and small incision are closed by the surgeon according to conventional surgical methods (denoted step "xvi").

According to the invention, the incision made in the pericardium can also be closed by the surgeon according to conventional surgical methods.

As reflected above, there is thus also provided a method for accessing intrathoracic biological tissue structures of a subject comprising the steps of:

(i) providing, assembling and preparing thoracic structure access system 100 as described above;

(ii) making a xiphoid incision 6 at a transxiphoid incision site 7;

(iii) positioning the thoracic structure access system 100 proximate the transxiphoid incision site 7, whereby first biological tissue, e.g., 5b, is engaged with the at least one tissue retractor member 30a of the tissue retention arm assembly 8a proximate the xiphoid incision 6 and opposing second biological tissue, e.g., 5a, is engaged with the at least one tissue retractor arm sub-assembly 20 of the tissue retractor arm assembly 9a proximate the xiphoid incision 6; and (iv) rotating the handle assembly 80 of the ratchet assembly 70a in a first handle direction, i.e., actuating the ratchet assembly 70a, whereby the ratchet assembly 70a laterally translates the first ratchet sub-assembly 72a of the thoracic structure access system 100 and, thereby, the tissue retractor arm assembly 9a in a first pre-determined direction substantially parallel to the longitudinal axis $LA_3$ of the ratchet assembly 70a and the tissue retractor arm assembly 9a and the tissue retention arm assembly 8a and, thereby, the first and second biological tissue proximate the xiphoid incision 6 are disposed a spaced distance apart and an open access space 202 at the transxiphoid incision site 7 is provided.

According to the invention, the aforedescribed minimally invasive CAGB (and OPCAB) procedure can similarly be performed with thoracic structure access system 102.

In at least one embodiment, the steps to perform the aforedescribed minimally invasive CAGB procedure similarly comprise steps ii, iii, iv, ix, x, xi, xii, xiii, xiv and xvi above. However, as indicated below, steps i, v, vi, vii, viii and xv now comprise the following:

Step i—Providing, Assembling and Preparing Thoracic Structure Access System 102

Referring to FIG. 11A, the thoracic structure access system is assembled as follows:

(a) the elongated arm member 10a is releasably engaged to the first interconnector member 40, as described above;

(b) the coupling member 50d is releasably engaged to the first interconnector member 40, as described above;

(c) the coupling member 50d is also releasably engaged to ratchet sub-assembly 72d, as described above;

(d) the elongated arm member 10b is releasably engaged to the second interconnector member 40, as described above;

(e) the coupling member 50e is releasably engaged to the second interconnector member 40, as described above;

(f) the coupling member 50e is also releasably engaged to ratchet sub-assembly 72c, as described above;

(g) the tissue retractor member 30b is releasably engaged to elongated arm member 10a and the tissue retractor member 30a is releasably engaged to elongated arm member 10b, as described above, to assemble retractor and retention arm assemblies 8b, 9b, respectively;

(h) in some embodiments of the invention, wherein the handle assembly 80 of the second ratchet assembly 70b is not an integral component of the first ratchet sub-assembly 72c, the handle assembly 80 is rotatably seated in guide hole 78 of the first ratchet sub-assembly 72c, as described above;

(i) the distal end 76b of toothed crossbar 74 is slidably translated into slot 71 of first ratchet sub-assembly 72c; and (j) retractor and retention arm assemblies 9b, 8b are then releasably engaged to first and second ratchet sub-assemblies 72c, 72d, respectively, as described above, to complete the assembly of thoracic structure access system 102.

According to the invention, the seminal components of thoracic structure access system 102 of the invention can similarly be assembled in any suitable order.

Step v—Positioning the Thoracic Structure Access System 102

After the endoscope is routed into and through the incision made in the pericardium, i.e., step iv above, the thoracic structure access system 102 is positioned proximate the transxiphoid incision site 7.

Step vi—Positioning the Retention Arm Assembly Proximate First Biological Tissue After the thoracic structure access system 102 is positioned proximate the transxiphoid incision site 7, i.e., new step v above, the retention arm assembly 8b is positioned proximate first biological tissue proximate the transxiphoid incision site 7, i.e., thoracic tissue portion 5b, in a manner such that a section of thoracic tissue portion 5b can be releasably engaged to tissue retractor member 30b.

Step vii—Positioning the Retractor Arm Assembly Proximate Second Biological Tissue After the retention arm assembly 8b is positioned proximate first biological tissue proximate the transxiphoid incision site 7, i.e., new step vi above, the retractor arm assembly 9b is positioned proximate opposed second biological tissue proximate the transxiphoid incision site 7, i.e., thoracic tissue portion 5a, in a manner such that a section of thoracic tissue portion 5a can be releasably engaged to tissue retractor member 30a.

Step viii—Providing the Access Space at the Transxiphoid Incision Site

After the retractor arm assembly 9b is positioned proximate opposed second biological tissue proximate the transxiphoid incision site 7, i.e., new step vii above, the drive handle 82 of handle assembly 80 is actuated, i.e., rotated in a first direction, to laterally translate ratchet sub-assembly 72c along toothed crossbar 74 in a first pre-determined direction toward the distal end 76d of crossbar 74 with retractor arm assembly 9b operatively connected thereto, whereby the retention and retractor arm assemblies 8b, 9b spread and lift at least the lower portion 4 of the sternum 200 (by applying opposing forces to a section of thoracic tissue portion 5b and a section of thoracic tissue portion 5a and, thereby, offsetting thoracic tissue portion 5b and thoracic tissue portion 5a) to provide an access space 202 at the transxiphoid incision site 7.

Step xv—Closing the Access Space

After the endoscope is employed to check the anastomotic connections for kinking or leaks, to check the position of the drainage tube, and to check the integrity of the pleural tissue, i.e., step xiv above, the drive handle 82 of handle assembly 80 is actuated, i.e., rotated in a second direction, to laterally translate ratchet sub-assembly 72c and, thereby retractor arm assembly 9b along toothed crossbar 74 in a second pre-determined direction toward the retractor sub-assembly 72d, whereby the force(s)/pressures(s) on the lower portion 4 of the sternum 200 (applied by the retractor arm and retention arm assemblies 9b, 8b on a section of thoracic tissue portion 5a and a section of thoracic tissue portion 5b, respectively) are relieved and to close access space 202.

In some embodiments of the invention, wherein the thoracic structure access system 102 comprises retractor and retention arm assemblies 9c and 8c, step i, i.e., Providing, Assembling and Preparing Thoracic Structure Access System 102, comprises the following:

(a) the retractor arm assembly 9c is releasably engaged to ratchet sub-assembly 72c, as described above;

(b) the retention arm assembly 8c is releasably engaged to ratchet sub-assembly 72d, as described above; and (c) at least one tissue retractor member 30b is releasably engaged to the retention arm assembly 8c and at least one tissue retractor member 30a is releasably engaged to the retractor arm assembly 9c.

As reflected above, there is thus provided a further method for accessing intrathoracic biological tissue structures of a subject comprising the steps of:

(i) providing, assembling and preparing one of the aforementioned embodiments of thoracic structure access system 102 as described above;

(ii) making a xiphoid incision 6 at a transxiphoid incision site 7;

(iii) positioning the thoracic structure access system 102 proximate the transxiphoid incision site 7, whereby first biological tissue, e.g., 5b, is engaged with the at least one tissue retractor member 30b of the tissue retention arm assembly 8b proximate the xiphoid incision 6 and opposing second biological tissue, e.g., 5a, is engaged with the at least one tissue retractor member 30a of the tissue retractor arm assembly 9b proximate the xiphoid incision 6; and (iv) rotating the handle assembly 80 of the ratchet assembly 70b in a first handle direction, whereby the ratchet assembly 70b laterally translates the first ratchet sub-assembly 72c of the thoracic structure access system 102 and, thereby, the tissue retractor arm assembly 9b in a first pre-determined direction substantially parallel to the longitudinal axis $LA_3$ of the ratchet assembly 70b and the tissue retractor arm assembly 9b and the tissue retention arm assembly 8b and, thereby, the first and second biological tissue proximate the xiphoid incision 6 are disposed a spaced distance apart and an open access space 202 at the transxiphoid incision site 7 is provided.

As indicated above and reflected in the above procedure, when the thoracic structure access apparatus and systems of the invention are employed to access intrathoracic biological structures, the apparatus and systems substantially reduce biological tissue trauma by enabling optimal placement of biological tissue pressure points proximate a transxiphoid incision site and reducing the force/pressure applied to biological tissue structures proximate to the positions of biological tissue pressure points.

In a preferred embodiment, the thoracic structure access apparatus and systems of the invention also avoid applying force/pressure to inferior regions of a subject's costal cartilage, or shear stress to the pleural tissue of a subject, thus, sparing the costal cartilage and the pleural tissue, which results in a substantially shorter post-operative recovery time for a subject.

As will readily be appreciated by one having ordinary skill in the art, the present invention thus provides numerous advantages compared to prior art methods and systems for accessing intrathoracic biological tissue (and intrathoracic tissue structures). Among the advantages are the following:

The provision of thoracic structure access systems that can be readily employed to facilitate various thoracic surgical procedures; particularly, CABG and OPCAB procedures, in a simple and economical manner.

The provision of thoracic structure access systems that can be readily employed to substantially reduce or eliminate trauma of biological tissue associated with tissue retraction during a surgical procedure; particularly, a CABG and/or OPCAB procedure.

The provision of thoracic structure access systems that can be readily employed to provide access to cardiovascular structures, including a beating heart, during CABG and OPCAB procedures in a minimally invasive manner.

The provision of thoracic structure access systems that can be readily employed to facilitate CABG and OPCAB procedures via a simple incision at a transxiphoid incision site and, hence, without fully transecting the sternum, i.e., performing a full sternotomy, or performing a thoracotomy.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for accessing intrathoracic biological tissue structures of a subject, said subject comprising a sternum, xiphoid process, and thoracic cage, comprising the steps of:

(i) providing a thoracic access system configured and adapted to provide access to intrathoracic structures through a xiphoid incision proximate a xiphoid process and without fully transecting a sternum, said thoracic access system comprising a tissue retractor arm assembly, a tissue retention arm assembly, and a ratchet assembly, said tissue retractor arm assembly comprising a first elongated arm member, a first coupling member, and a first interconnector member disposed between and rotatably connecting said first elongated arm member and said first coupling member, said first elongated arm member comprising a first longitudinal axis, said first coupling member comprising a second longitudinal axis, said tissue retention arm assembly comprising a second elongated arm member, a second coupling member, and a second interconnector member disposed between and rotatably connecting said second elongated arm member and said second coupling member, said second elongated arm member comprising a third longitudinal axis, said second coupling member comprising a fourth longitudinal axis, said ratchet assembly comprising a fifth longitudinal axis, said ratchet assembly comprising a crossbar, a first ratchet sub-assembly, a second ratchet sub-assembly, and a handle assembly, said first ratchet assembly comprising a first pinion assembly, said second ratchet assembly comprising a second pinion assembly, said first ratchet sub-assembly slideably engaged to said crossbar and adapted to rotatably engage said first coupling member, whereby said first pinion assembly is in communication with said first coupling member, wherein, when said first pinion assembly is rotated, said first coupling member rotates about said second longitudinal axis of said first coupling member and induces rotation of said first interconnector member and, thereby, first angular articulation of said first elongated arm member relative to said first longitudinal axis of said first elongated arm member, said second ratchet sub-assembly engaged to said crossbar and adapted to rotatably engage said second coupling member, whereby said second pinion assembly is in communication with said second coupling member, wherein, when said first pinion assembly is rotated, said second coupling member rotates about said fourth longitudinal axis of said second coupling member and induces rotation of said second interconnector member and, thereby, second angular articulation of said second elongated arm member relative to said third longitudinal axis of said second elongated arm member, said handle assembly operatively connected to said first ratchet sub-assembly and adapted to induce first lateral motion of said first ratchet sub-assembly and, thereby, said tissue retractor arm assembly in a plane substantially parallel to said fifth longitudinal axis of said ratchet assembly, whereby said tissue retractor arm assembly transitions over a plurality of retractor arm assembly tissue engaging positions when said first coupling member of said tissue retractor arm assembly is said rotatably connected to said first ratchet sub-assembly, said first elongated arm member of said tissue retractor arm assembly comprising at least a first tissue retractor member configured and adapted to releasably engage first biological tissue proximate said xiphoid incision when said tissue retractor arm assembly is in at least a first retractor arm assembly tissue engaging position of said plurality of retractor arm assembly tissue engaging positions, said second elongated arm member of said tissue retention arm assembly comprising at least a second tissue retractor member configured and adapted to releasably engage second biological tissue proximate said xiphoid incision when said tissue retention arm assembly is in at least a first retention arm assembly tissue engaging position and said tissue retractor arm assembly is in said at least a first retractor arm assembly tissue engaging position, said tissue retractor arm assembly and said tissue retention arm assembly, when said rotatably connected to said ratchet assembly and said engaged to said first and second biological tissue, being configured and adapted to jointly and uniformly lift opposing portions of a thoracic cage;

(ii) making a first xiphoid incision proximate said subject's xiphoid process, wherein said subject's sternum is not fully transected;

(iii) positioning said thoracic access system proximate said first xiphoid incision, whereby third biological tissue proximate said first xiphoid incision is engaged with said tissue retractor arm assembly and fourth biological tissue proximate said first xiphoid incision is engaged with said tissue retention arm assembly, said third biological tissue being disposed substantially opposite said fourth biological tissue;

(iv) rotating said handle assembly of said ratchet assembly in a first handle direction, whereby said ratchet assembly laterally translates said first ratchet sub-assembly and, thereby, said tissue retractor arm assembly in said at least first lateral motion of said tissue retractor arm assembly, wherein said third and fourth biological tissue proximate said first xiphoid incision are disposed a spaced distance apart and an open access space proximate said subject's xiphoid process is provided; and (v) rotating said first and second pinion assemblies, wherein said first angular articulation of said first elongated arm member and, thereby, said tissue retractor arm assembly is induced and said second angular articulation of said second elongated arm member and, thereby, said tissue retention arm assembly is induced, whereby first and second opposing portions of said subject's thoracic cage are lifted.

\* \* \* \* \*